US008717569B2

(12) United States Patent
Lo et al.

(10) Patent No.: US 8,717,569 B2
(45) Date of Patent: May 6, 2014

(54) APPARATUS AND METHOD FOR IMPROVED OPTICAL DETECTION OF PARTICLES IN FLUID

(75) Inventors: Yu-Hwa Lo, San Diego, CA (US);
Victor Jie Lien, San Diego, CA (US);
Chun Hao Randy Chen, Arcadia, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/605,925

(22) Filed: Sep. 6, 2012

(65) Prior Publication Data

US 2013/0004987 A1 Jan. 3, 2013

Related U.S. Application Data

(62) Division of application No. 12/091,414, filed as application No. PCT/US2006/060313 on Oct. 27, 2006, now Pat. No. 8,270,781.

(60) Provisional application No. 60/731,551, filed on Oct. 28, 2005.

(51) Int. Cl.
G01N 21/00 (2006.01)
(52) U.S. Cl.
USPC .............................................. 356/436; 422/50
(58) Field of Classification Search
USPC ............... 250/458.1, 461.2; 385/12; 356/318, 356/436; 600/310, 323; 435/29
See application file for complete search history.

(56) References Cited

U.S. PATENT DOCUMENTS

| 6,909,824 | B1 | 6/2005 | Messica et al. |
| 7,245,379 | B2 | 7/2007 | Schwabe |
| 7,746,466 | B2 | 6/2010 | Godin et al. |
| 2004/0072278 | A1 | 4/2004 | Chou et al. |
| 2005/0068536 | A1* | 3/2005 | Schwabe ........................ 356/436 |
| 2005/0112541 | A1 | 5/2005 | Durack et al. |
| 2006/0197033 | A1* | 9/2006 | Hairston et al. ............ 250/458.1 |

(Continued)

FOREIGN PATENT DOCUMENTS

| WO | 94/05775 A1 | 3/1994 |
| WO | 2010/104993 A2 | 9/2010 |

OTHER PUBLICATIONS

Zhang et al. Biomedical Microdevices 6:1, 11-21, 2004.*

(Continued)

Primary Examiner — Sally Merkling
(74) Attorney, Agent, or Firm — Perkins Coie LLP

(57) ABSTRACT

A number of fluidic-photonic devices for allowing optical detection, systems employing such devices, and related methods of operation and fabrication of such devices are disclosed herein. In at least some embodiments, the devices can serve as flow cytometry devices and/or employ microfluidic channels. Also, in at least some embodiments, the devices are fluidic-photonic integrated circuit (FPIC) devices that employ both fluidic channels and one or more waveguides capable of receiving and/or delivering light, and that can be fabricated using polymeric materials. The fluidic-photonic devices in at least some embodiments are capable of functionality such as on-chip excitation, time-of-flight measurement, and can experience enhanced fluorescence detection sensitivity. In at least some embodiments, the devices employ detection waveguides that are joined by way of a waveguide demultiplexer. In additional embodiments, a variety of techniques can be used to process information received via the waveguides, including an iterative cross-correlation process.

18 Claims, 12 Drawing Sheets

(56) References Cited

U.S. PATENT DOCUMENTS

2007/0117086 A1    5/2007    Evans et al.
2007/0140638 A1    6/2007    Yang et al.
2009/0027666 A1    1/2009    Godin et al.
2012/0078531 A1    3/2012    Lo et al.

OTHER PUBLICATIONS

Lien, V., et al., "Fluidic Photonic Integrated Circuit for In-Line Detection," Applied Physics Letters, 87(19):194106(1-3), Nov. 2005.
Chen, C., et al., "Microfluidic cell sorter with integrated piezoelectric actuator," Biomedical Microdevices, 11 (6):1223-1231, Aug. 2009.
Cho, S., et al., "Micro-fabricated Fluorescence-Activated Cell Sorter," Annual International Conference of the IEEE Engineering in Medicine and Biology Society, pp. 1075-1078, Sep. 3-6, 2009.
Cho, S., et al., "Microfluidic Photonic Integrated Circuits," Optoelectronic Materials and Devices, vol. 7135, pp. 1-17, Jan. 2008.
Cho, S., et al., "Optofluidic Waveguides in Teflon AF-Coated PDMS Microfluidic Channels," IEEE Photonics Technology Letters, 21(15)1057-1059, Aug. 1, 2009.
Fu, A.Y., et al., A Microfabricated Fluorescence-Activated Cell Sorter, Nature Biotechnology, vol. 17, pp. 1109-1111, Nov. 1999.
Godin, J., et al., "Microfluidics and photonics for Bio-System-on-a-Chip: A review of advancements in technology towards a microfluidic flow cytometry chip," Journal of Biophotonics, 1(5)355-376, Oct. 2008.

International Search Report and Written Opinion mailed on Nov. 1, 2007 for International Application No. PCT/US2006/060313, filed Oct. 27, 2006 (4 pages).
International Search Report and Written Opinion mailed on Oct. 26, 2010 for International Application No. PCT/US2010/026884, filed Mar. 10, 2010 (10 pages).
Lee, G.-B., et al., "Micro Flow Cytometers with Buried SU-8/SOG Optical Waveguides," Sensors and Actuators A: Physical, 103(1):165-170, Jan. 2003.
Lien, V., et al., "A Prealigned Process of Integrating Optical Waveguides With Microfluidic Devices," IEEE Photonics Technology Letters, 16(6):1525-1527, Jun. 2004.
Lien, V., et al., "High-Sensitivity Cytometric Detection Using Fluidic-Photonic Integrated Circuits with Array Waveguides," IEEE Journal of Selected Topics in Quantum Electronics, 11(4):827-834, Jul./Aug. 2005.
Lien, V., et al., "Microfluidic-photonic-dielectrophoretic integrated circuits for biophotonic sensing," The 17th Annual Meeting of the IEEE Lasers and Electro-Optics Society, vol. 2, pp. 533-534, Nov. 2004.
Tung, Y.-C., et al., "PDMS-based opto-fluidic micro flow cytometer with two-color, multi-angle fluorescence detection capability using PIN photodiodes," Sensors and Actuators B, 98(2-3):356-367, Mar. 2004.

* cited by examiner

APPARATUS AND METHOD FOR IMPROVED OPTICAL DETECTION OF PARTICLES IN FLUID

CROSS-REFERENCE TO RELATED APPLICATIONS

This application is a divisional application and claims priority to U.S. patent application Ser. No. 12/091,414, filed on Apr. 24, 2008, which is a U.S. National Stage application under 35 U.S.C. §371 of International Patent Application No. PCT/US2006/060313, filed on Oct. 27, 2006, which claims benefit of priority of U.S. Provisional Patent Application No. 60/731,551, filed on Oct. 28, 2005. The entire contents of the before-mentioned patent applications are incorporated by reference as part of the disclosure of this application.

STATEMENT REGARDING FEDERALLY SPONSORED RESEARCH OR DEVELOPMENT

This invention was made with United States Government support awarded by the following agencies: Air Force Office of Scientific Research (AFOSR) Grant No. F49620-02-1-0288. The United States Government has certain rights in this invention.

FIELD OF THE INVENTION

The present invention relates to systems and methods for optical detection and, more particularly, to systems and methods for detecting small objects or particles such as cells or DNA.

BACKGROUND OF THE INVENTION

Over a period of nearly five decades, flow cytometry has evolved from a simple technique for counting suspended particles (e.g., analytes, cells or DNA) in fluid into a highly sophisticated and versatile technique that is critical to clinical diagnosis and fundamental biomedical research. Early efforts in the development of flow cytometry focused upon the attainment of a stable flow system able to transport particles, without disturbance by any alien aerosol, to regions of laser beam illumination for optical interrogation via fluorescence or light scattering. A standard approach for today's flow cytometers is to create a laminar sheath flow in a transparent capillary tube to minimize noise due to fluctuations in position and propagation speed of the particles. Besides such improvements in controlling particle flow and in flow cytometry instrumentation generally, significant progress has also been made with respect to other aspects of flow cytometry, for example, with respect to the methods of cell preparation, new fluorescent dyes and new markers of cell properties.

These technological advances in flow cytometry have made it possible to use flow cytometers in a variety of areas. For example, flow cytometers are now used for analyzing white blood cells in AIDS patients. Also for example, flow cytometers are now employed in performing cancer diagnosis and stem cell sorting. Indeed, flow cytometry is now widely recognized as an important clinical and research tool. However, even though the size of a flow cytometer has been reduced from a piece of equipment occupying an entire room to a table top system with ever increasing functionality and performance, flow cytometers continue to cost between $150K and $1M, and consequently remain a tool affordable only by major medical centers and laboratories. Size and price reduction by orders of magnitude (e.g. 1000 times) are necessary to make flow cytometers a prevailing diagnosis tool that can be afforded by more hospitals and medical practitioners around the world.

One technique that holds promise for miniaturizing flow cytometers is the use of microfabricated flow cells, enabled by advances in microfluidics. Integrated microfluidic chips that perform a variety of functions for chemical analysis and biological screening have found wide applications in the pharmaceutical industry and have accelerated the progress of research in biotechnology. Several research groups have demonstrated the ability to manipulate cells and micro-particles in microfluidic devices using the effects of fluidic pressure, dielectrophoresis, optical trapping, and electro-osmosis. More particularly, the introduction of microfabricated electrodes in the fluidic channels of microfluidic devices can facilitate the optical detection of particles by controlling and manipulating the positions, angles, and populations of the particles in microfluidic channels via the dielectrophoretic effect.

There are several reasons that make these results particularly relevant to the development of compact flow cytometers. First, biological cell sizes fit well with the dimensions of the microfluidic devices that can be easily and precisely fabricated using microfabrication techniques such as lithography and molding. Second, microfluidic devices tend to support laminar flow, making the flow control simpler and fluid transport highly efficient. Third, micro-scale integration allows more functionality (e.g. pumps, valves and switches) to be incorporated into the device. Finally, two-dimensional or even three-dimensional array structures can be fabricated to enhance the performance of the system and alleviate the limit of device throughput.

Although rapid progress has been made in microfluidics that is applicable to flow cytometry, the scheme of optical detection employed in flow cytometry has not experienced similarly important advances or changes. In particular, while the hardware utilized in performing optical detection has continued to evolve, resulting in more advanced lasers, more sensitive detectors, and superior optical mechanical components, there nevertheless has not been any paradigm shift in terms of the manner in which optical detection is performed in flow cytometry. As a result, the expensive and bulky optical setup currently necessary for fluorescence detection threatens to become a bottleneck restricting the realization of compact, low-cost flow cytometers. Additionally, the relatively high cost of lasers and light detectors for use in flow cytometry is further exacerbated when one reduces the size of the overall system.

For at least these reasons, it would be advantageous if an improved optical detector, optical detection scheme or optical detection method could be developed for use in detecting small objects or particles such as cells or DNA, as could be used for, among other things, performing flow cytometry and related techniques. More particularly, it would be advantageous if, in at least some embodiments, such an improved optical detector/detection scheme/method could be designed in which smaller (in terms of size and/or weight) optical components could be employed. Additionally, it would be advantageous if, in at least some embodiments, simpler, less expensive components could be employed for the purposes of generating and/or sensing light.

BRIEF SUMMARY OF THE INVENTION

The present inventors have recognized the desirability of achieving improved photonic designs and technologies for detecting small objects or particles, for use in various applications such as flow cytometry involving the use of microfluidic components. For example, the present inventors have recognized the desirability of providing a cost effective solution to the problem of fluorescence (and side scattering) detection in flow cytometry and, more particularly, have recognized the importance of at least one of (a) integrating optical components with fluidic circuits to reduce the size and weight of the overall system, and (b) developing innovative architectures of photonic circuits to achieve desired levels of sensitivity without the need for expensive components such as lasers (e.g., main frame lasers) and/or ultra sensitive detectors (e.g., photomultiplier tubes (PMTs)).

In accordance with at least some embodiments of the present invention, to achieve such goals the present inventors propose a microfluidic-photonic integrated circuit optical interrogation device that can be utilized as a microfabricated flow cytometer. The device includes a photonic circuit integrated monolithically with the microfluidic channels such that the optical interrogation zones are in the proximity of and well aligned to the optical waveguides that collect the fluorescence and/or scattering light signals. The use of such a waveguide approach to replace free-space optics eliminates the needs for lenses and precision mechanics for optical alignment, making significant size and weight reduction possible. The device can be fabricated using a fluidic-photonic integrated circuit (FPIC) process.

In at least some such embodiments, multiple waveguides are employed to form an array waveguide structure so that, along the direction of flow, a particle (e.g., an analyte, cell or segment of DNA) will pass a series of waveguide-defined optical interrogation zones, each producing a signal that is correlated in time and space to the others. In one example of such an embodiment, an array of eight parallel waveguides is employed so that the signal produced by a particle will be detected eight times. At the detection end, an array of eight detectors can be employed or, alternatively, it is possible to combine the eight waveguides into a single output waveguide and use only a single detector (or, also alternatively, more than one but less than eight detectors can be employed). For a single detector approach, the signals from the eight waveguides can be multiplexed in the time domain, with a time delay of the demultiplexed operation being set equal to the transit time of the particle as it passes between adjacent waveguides.

In at least some embodiments, the present invention relates to a device that includes a fluidic channel capable of conducting a fluid containing at least one particle, a source of electromagnetic radiation arranged to provide the electromagnetic radiation into the fluidic channel to interact with the at least one particle contained within the fluid as the fluid is conducted by the fluidic channel, and a first plurality of optical waveguides having respectively a plurality of ends positioned along the fluidic channel. The optical waveguides receive at least some of the electromagnetic radiation after the electromagnetic radiation has interacted with the at least one particle.

Additionally, in at least some embodiments, the present invention relates to a fluidic-photonic integrated circuit (FPIC) device that includes a microfluidic channel, means for exciting a material within the microfluidic channel, and a first optical waveguide for receiving electromagnetic radiation as a result of the exciting of the material. Information regarding the material is detected based upon the received electromagnetic radiation.

Further, in at least some embodiments, the present invention relates to a method of manufacturing a fluidic-photonic integrated circuit (FPIC) device. The method includes casting pre-polymer onto a photo-lithographically patterned mold, thermally-curing the pre-polymer, and demolding a first piece of thermally-cured polymer from the mold. The method also includes bonding the first piece to a second piece of polymer material to form a fluidic channel, and implementing the fluidic channel in relation to a further structure capable of receiving and guiding electromagnetic radiation away from the fluidic channel.

Additionally, in at least some embodiments, the present invention relates to a method of obtaining information regarding at least one particle suspended within a flowing fluid. The method includes applying incident light to the fluid and to the at least one particle suspended within the fluid as the fluid flows through a fluidic channel, and guiding scattered or fluorescent light resulting from an interaction between the incident light and the at least one particle by way of a plurality of optical waveguides extending away from the fluidic channel to at least one detection device. The method further includes deriving at least one signal at the at least one detection device based upon the guided, scattered or fluorescent light, and performing a calculation based upon the at least one signal resulting in the information, the information being indicative of at least one characteristic of the at least one particle.

DETAILED DESCRIPTION OF THE PREFERRED EMBODIMENT

As described in detail below, the present invention is intended to encompass a variety of different embodiments of microfluidic-photonic integrated circuits and similar devices, as well as systems that implement those integrated circuits and devices. Such devices can be employed for a variety of purposes including, for example, to detect the presence of biological particles such as cells and DNA or other particles, and/or in various applications such as flow cytometry and other techniques. Additionally, the present invention is intended to encompass various methods of operating and manufacturing such integrated circuits and other devices (and/or systems that implement those integrated circuits and devices). In at least some embodiments, for example, microfluidic-photonic-dielectrophoretic integrated circuits can be fabricated by way of a process involving micro-molding, polymer bonding, and channel waveguides with capillary filling. At least some of the circuits described herein can be considered to represent a new class of circuits particularly attractive to lab-on-a-chip and biomedical applications.

Figure 1A:
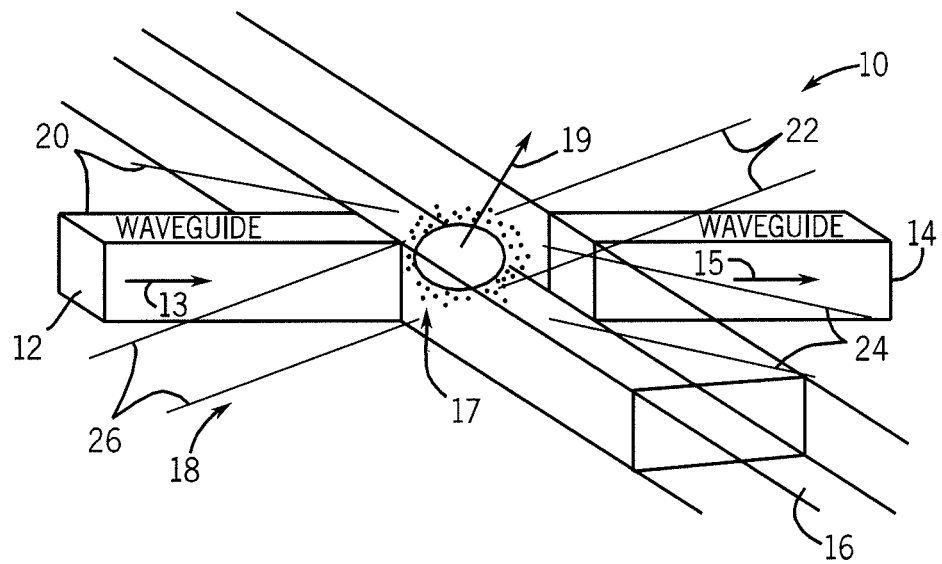
FIGS. 1(a) and 1(b) respectively provide a schematic, side perspective view and a top plan view of an exemplary integrated fluidic-photonic device having a fluidic channel, optical waveguide, and a dielectrophoretic (DEP) cage, in accordance with at least some embodiments of the present invention.
Figure 1B:
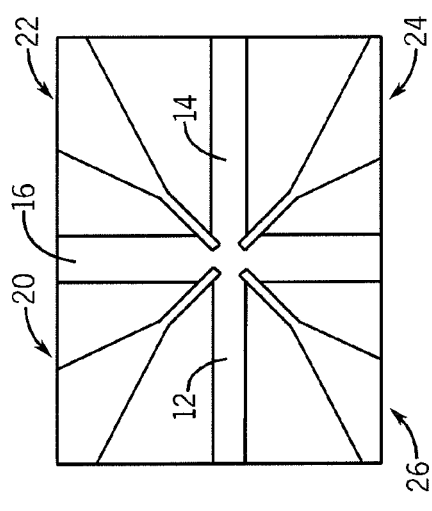

Referring to FIGS. 1(a) and 1(b), a schematic, side perspective view and a top plan view are provided of a first exemplary microfluidic-photonic integrated circuit device 10 that is capable of allowing fluorescent excitation and detection to be performed. Although capable of being employed in various environments, the device 10 in at least some cases is intended to perform on-chip optical detection of biological particulate material or analytes such as single cell(s) and/or small aggregations of DNA. As shown particularly in FIG. 1(a), the device 10 includes first and second waveguides 12 and 14, respectively, that are aligned with one another and extend away from each other. Further as shown, the first and second waveguides 12, 14 respectively extend up to opposite sides of a fluidic channel 16 that extends perpendicularly between the waveguides. Light passing through the first waveguide 12 along a direction generally indicated by an arrow 13 passes through a target region 17 of the fluidic channel 16, where it can interact with particulate material 19 flowing through the target region. Some or all (or possibly none) of the light, depending upon the light's interaction with the particulate material, then passes through the second waveguide 14 along a direction generally indicated by an arrow 15.

Additionally, the device 10 also includes a dielectrophoretic electric cage 18 formed by four pairs of diagonally-arranged electrodes 20, 22, 24 and 26, respectively, where each pair of electrodes includes an upper and a lower electrode as illustrated in FIG. 1(a). The dielectrophoretic electric cage 18 is designed to trap and rotate the target particular material electrically. The trapped object tends to reside at the position in the fluid where the potential energy is lowest. If an ac voltage is applied to the four pairs of electrodes 20, 22, 24 and 26 with a phase difference (e.g., with approximately 90-degree phase differences between each adjacent pair of electrodes), then the trapped object can obtain angular momentum and spin while it is trapped.

Referring additionally to FIG. 1(b), the top view of the device 10 further illustrates the relative arrangement of the integrated pairs of electrodes 20, 22, 24 and 26, the waveguides 12, 14 and the fluidic channel 16. As shown, each of the electrodes 20, 22, 24 and 26 extends at 45 degree angles relative to its respective neighboring one of the waveguides 12, 14 and relative to the fluidic channel 16, so as to form an "X" arrangement overlapping a "+" arrangement formed by the waveguides and fluidic channel. Also as shown, the electrodes 20, 22, 24, and 26 protrude slightly into the target region 17 of the fluidic channel 16. It should be noted that the fluidic channel 16, waveguides 12, 14 and electrodes 20, 22, 24 and 26 in the present embodiment are small or microscopic in size, typically having a smallest feature size between 5 and 50 micrometers.

Figure 2C:
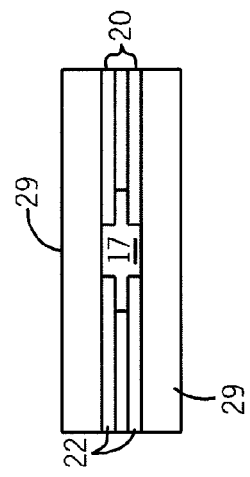
FIGS. 2(a)-(c) illustrate steps of an exemplary process of manufacturing the device of FIGS. 1(a)-(b) having DEP electrodes integrated with a microfluidic channel.
Figure 2B:
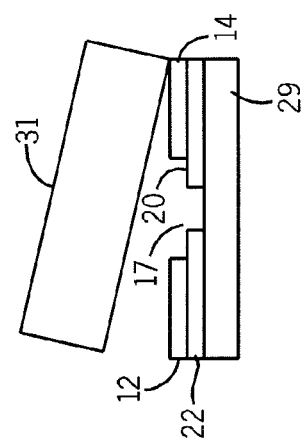
Figure 2A:
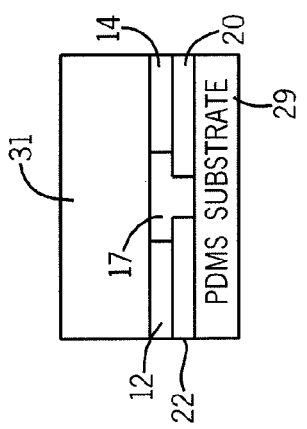

A variety of processes can be implemented in order to manufacture or otherwise form the device 10 of FIGS. 1(a)-(b). Referring to FIGS. 2(a)-(c), steps of one exemplary process for fabricating the device 10 are shown. In particular, a self-aligned process is employed to form the fluidic channel 16 and waveguides 12, 14 between the four pairs of electrodes 20-26 in a manner such that the electrodes of each pair are parallel to one another. As shown in FIG. 2(a), in a first step the lower electrode of each pair of the electrodes 20-26 are all formed atop a polydimethylsiloxane (PDMS) substrate 29 (more particularly, two electrodes from the first and second pairs of electrodes 20 and 22 are shown). Atop the four lower electrodes are then positioned the waveguides 12, 14, and atop the waveguides is positioned a handle wafer 31. The target region 17 of the fluidic channel 16 is within the space formed by the adjacent electrodes and waveguides. In the present embodiment, the electrodes are made from gold (Au), albeit other materials can be used in alternate embodiments.

Once the structures have been assembled as shown in FIG. 2(a), and in particular once the lower electrodes have been formed by way of that step, the handle wafer 31 is delaminated from atop the waveguides 12, 14, at a step shown in FIG. 2(b). The removal of the handle wafer allows for the upper electrodes of each of the pairs of electrodes to be formed above the waveguides 12, 14. It is desirable that the upper electrodes and lower electrodes of each pair of electrodes 20-26 be aligned (e.g., parallel) with each other, and that the set of four upper electrodes and the set of four lower electrodes be respectively formed on two different planes on both (opposite) sides of the fluidic channel. To achieve such alignment, the addition of the upper electrodes of each pair, which can be formed within an electrode-patterned substrate can involve the use of an optical mechanical alignment tool such as a contact mask aligner or a wafer bonder. FIG. 2(c) shows the upper electrodes to be assembled atop the waveguides 12, 14, and additionally shows another PDMS substrate 29 to be positioned atop the upper electrodes. Thus, the target region 17 is entirely enclosed within the waveguides 12, 14, the pairs of electrodes 20-26 (only two pairs of which are shown in FIG. 2(c)), and the PDMS substrates 29, and the target region in particular has four pairs of electrodes around it forming the dielectrophoretic electric cage 18.

Figures 3A, 3B:
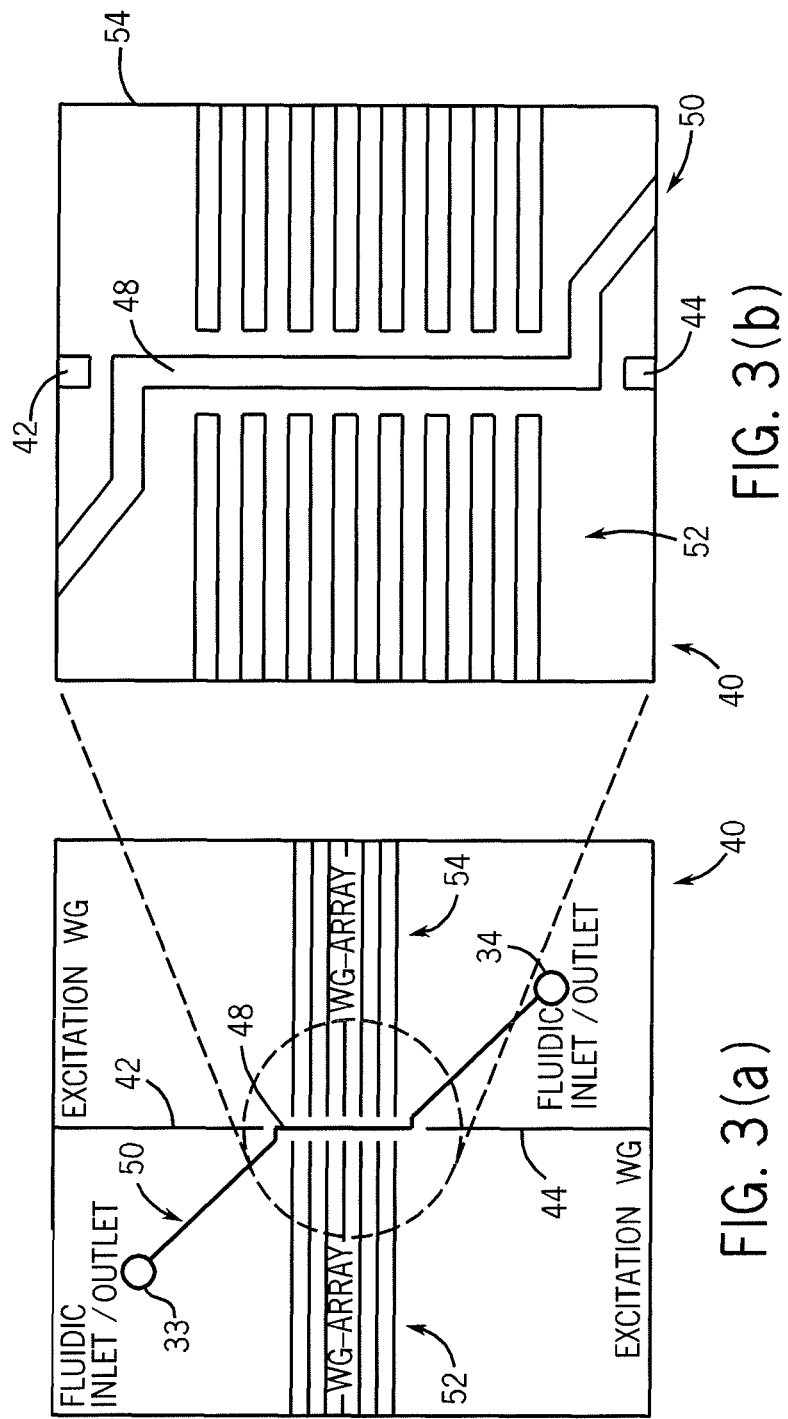
FIGS. 3(a) and (b) respectively show a schematic view and a side cross-sectional view of an exemplary fluidic-photonic integrated circuit device that can be employed in an improved optical detector in accordance with at least some embodiments of the present invention.
Figure 4:
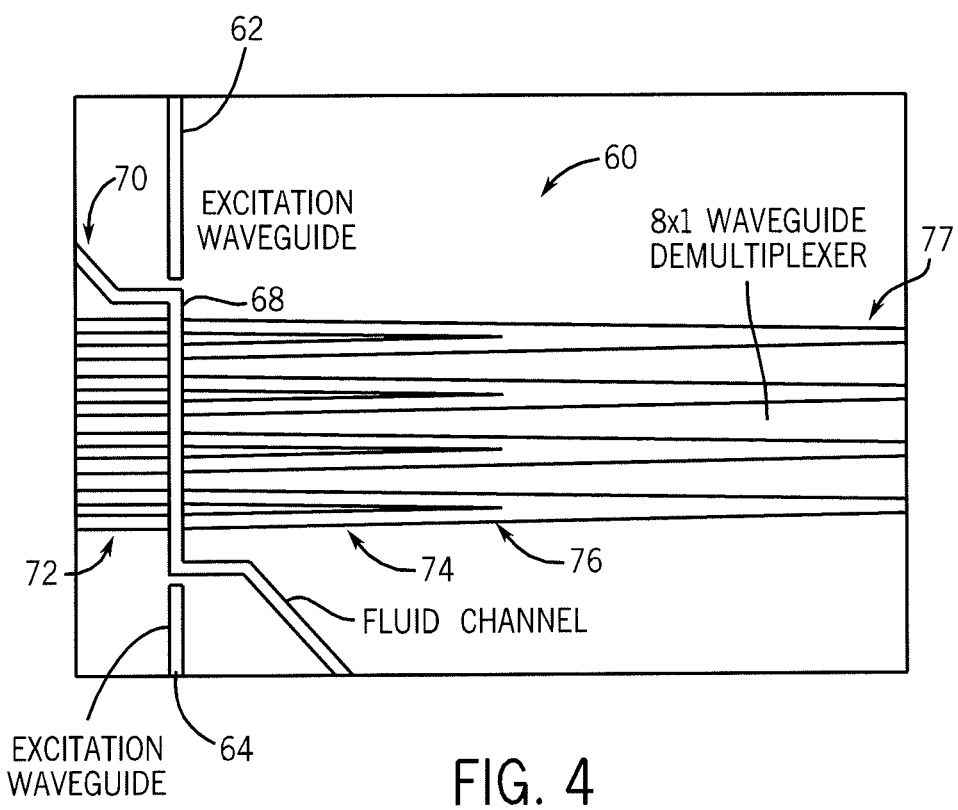
FIG. 4 shows a side cross-sectional view of an alternate embodiment of the fluidic-photonic integrated circuit device of FIGS. 3(a) and (b) in accordance with some other embodiments of the present invention.

Turning to FIGS. 3(a)-(b) and 4, additional embodiments of exemplary fluidic-photonic integrated circuit (FPIC) devices differing from that of FIGS. 1(a)-(b) are shown. The devices shown in FIGS. 3(a)-(b) and 4 in particular are guided wave photonic circuit devices that are more sophisticated in their operation than the device of FIGS. 1(a)-(b). Further, as with the device 10 of FIGS. 1(a)-(b), the devices shown in FIGS. 3(a)-(b) and 4 are fabricated to include microfluidic channels. Through the use of such microfluidic channels, the devices of FIGS. 3(a)-(b) and 4 can take a miniaturized form and are capable of delivering new functions including, for example, functions relating to the performance of flow cytometry, which is the workhorse for many biomedical applications. In particular, the devices allow for flow cytometry with relatively high signal reliability and sensitivity to be achieved, notwithstanding possible non-uniformities in the biological samples (or other sensed material) and/or complex flow patterns. In alternate embodiments, microfluidic channels need not be employed.

FIGS. 3(a) in particular shows a schematic diagram of a first FPIC device 40 that can be employed in an improved optical detector. FIG. 3(b) additionally shows a side cross-sectional view of a portion of the device 40 (e.g., in cut-away), while FIG. 4 shows a side cross-sectional view of a portion (e.g., in cut-away) of an alternate embodiment of the device 40, namely, a device 60. As shown, each of the devices 40, 60 of FIGS. 3(a)-(b) and 4 includes a respective fluidic channel 50, 70 including a respective vertical section 48, 68. As shown particularly in FIG. 3(a), the fluidic channel 50 of the device 40 extends between a first fluidic inlet/outlet 33 and a second fluidic inlet/outlet 34 (although not shown, the fluidic channel 70 of FIG. 4 also extends between two such inlets/outlets). Although the sections 48, 68 are shown to be vertically-oriented, the sections need not be oriented in this manner and instead could take on other orientations, such as horizontal orientations.

In addition to the fluidic channels 50, 70 and associated vertical sections 48, 68, each of the devices 40, 60 includes a respective first excitation waveguide 42, 62 and a respective second excitation waveguide 44, 64. The respective excitation waveguides of each respective device 40, 60 are aligned with, and extend in opposite directions from opposite ends of, the respective vertical section 48, 68 of the respective device. Thus, the waveguides 42, 44 are each aligned with the vertical section 48, with the first waveguide 42 extending upward away from the top of the vertical section and the second waveguide 44 extending downward from the bottom of the vertical section. Likewise, the waveguides 62, 64 are each aligned with the vertical section 68, with the first waveguide 62 extending upward away from the top of the vertical section and the second waveguide 64 extending downward from the bottom of the vertical section.

The waveguides 42, 44 of the device 40 and the waveguides 62, 64 of the device 60 each perform a similar function to that performed by the waveguides 12, 14 of the device 10 of FIGS. 1(a)-(b), namely, to cause excitation light to be directed toward (and possibly away from) a target region, where the target regions in these embodiments are the vertical section 48 and the vertical section 68, respectively. More particularly, the two waveguides 42, 44 and 62, 64 near the ends of the respective vertical sections 48, 68 of the respective fluidic channels 50, 70 deliver optical power for fluorescent excitation. The excitation light can come from various directions including from the top or the bottom of the device (e.g., as shown in FIGS. 3(a)-(b) and 4, similar to a microscope setup in terms of the direction of light passage through the microscope lens) as well as, in alternate embodiments, from other directions. The waveguides 42, 44, 62 and 64 as integrated on the devices 40, 60 in particular are able to provide convenient access of the excitation light at chosen wavelengths and in well-defined excitation directions. The well-defined excitation directions achieved through use of the waveguides 42, 44, 62 and 64 in particular facilitate the measurements of forward, side, and back scatterings of light as it encounters the sample particles or analytes flowing through the vertical sections 48, 68 of the fluidic channels 50, 70.

In addition to the respective pairs of excitation waveguides 42, 44 and 62, 64, each of the respective devices 40, 60 also includes a respective first array of horizontal waveguides 52, 72 and a respective second array of horizontal waveguides 54 and 74, respectively. The waveguides of the respective first and second arrays 52 and 54 respectively are arranged oppositely one another on left and right sides of the vertical section 48, and extend horizontally in opposite directions away from that vertical section, while the waveguides of the respective first and second arrays 62 and 64 respectively are arranged oppositely one another on left and right sides of the vertical section 68, and extend horizontally in opposite directions away from that vertical section. More particularly as shown, in the present embodiments, each of the arrays 52, 54, 72 and 74 has eight waveguides that extend parallel to one another horizontally away from the respective vertical section 48, 68, with each waveguide of each array being spaced apart from the neighboring waveguide(s) of the respective array by a predetermined amount of distance (e.g., 100 micrometers between the centers of neighboring waveguides). For each of the waveguides of the left-side arrays 52 and 72, there is a corresponding waveguide in the respective right-side array 54 and 74 that is aligned with that left-side array waveguide.

Each of the waveguides of the arrays 52, 54, 72 and 74 is capable of functioning as a detection waveguide capable of conducting/guiding light emanating from a respective one of the vertical sections 48, 68, and thus serves to allow for optical interrogation. In the present embodiments, optical detection occurs by sending excitation light into the vertical sections 48, 68 by way of one or both of the excitation waveguides 42, 44, 62, 64 associated with the respective vertical section, allowing that light to interact with and be scattered by the liquid-suspended sample particle(s) (e.g., cells, DNA or microparticles) flowing through the respective vertical section, and then sensing the amounts of scattered light that are received within and transmitted by the waveguides of the arrays 52, 54, 72 and 74. The light detected from the waveguides of the arrays 52, 54, 72 and 74 thus is indicative of the liquid-suspended sample particles (e.g., cells, DNA or microparticles) flowing through the respective fluidic channels 50, 70. As will be described in further detail below, the detection of light by way of multiple detection waveguides rather than merely one detection waveguide is particularly advantageous.

The dimensions of the fluidic channels 50, 70, the excitation waveguides 42, 44, 62 and 64 and the detection waveguides of the arrays 52, 54, 72, and 74 can vary depending upon the embodiment. In the present embodiments, the cross-sectional dimensions of the fluidic channels 50, 70 and particularly the vertical sections 48, 68 of those channels is $50 \times 50$ $\mu m^2$, although other cross-sectional dimensions are also possible. Additionally, the cross-sectional dimensions of each of the excitation waveguides 42, 44, 62 and 64 as well as each of the waveguides of the arrays 52, 54, 72 and 74 in the present embodiments further are $50 \times 50$ $\mu m^2$, although other dimensions are also possible. While in at least some embodiments, including the present embodiments, it is desirable that the waveguides have substantially the same cross-sectional dimensions (and shapes) as the corresponding fluidic channels, this need not be the case. Further, in the present embodiments of FIGS. 3(a)-(b) and 4, both the excitation waveguides 42, 44, 62, 64 and the detection waveguides of the arrays 52, 54, 72, 74 are multi-mode devices with a numerical aperture of 0.3.

The use of the arrays 52, 54, 72 and 74 of waveguides results is advantageous in several regards. Because each of the arrays 52, 54, 72 and 74 has eight parallel spaced-apart waveguides, each device 40, 60 has a capability of detecting a particle eight times as it passes through the respective vertical section 48, 68. More particularly, the use of the eight waveguides of each of the arrays 52, 54, 72 and 74, by providing eight detection points for the same target flying by, results in detected signals that have improved signal-to-noise ratios compared with conventional optical detection systems and in which randomness caused by Brownian motions is suppressed. In addition, the use of these arrays of waveguides allows for the performing of time-of-flight measurements, to determine the velocity of particles flying by, as well as allows for multi-label fluorescent detection with wavelength filters. Compared with single-point detection, the data that can be obtained using such multiple sampling points can provide rich information about the properties of a particle (or particles) under scrutiny, as well as the particle's interplay with the fluid, and the statistic behaviors under Brownian forces.

As discussed above, on the left sides of the respective vertical sections 48, 68 of the respective fluidic channels 50, 70 are positioned respective left-side arrays 52, 72, each of which has eight detection waveguides with separated outputs. Likewise, on the right sides of those vertical sections 48, 68 are positioned respective right-side arrays 54, 74, each of which also has eight detection waveguides. However, while the right-side array 54 of FIG. 3(*b*) has eight separated outputs associated with its respective eight detection waveguides, the right-side array 74 of FIG. 4 rather includes an 8×1 waveguide combiner or demultiplexer 76 such that all of the eight waveguides of that array eventually are merged to form a single output waveguide. That is, while the array 74 of the device 60 includes eight horizontal detection waveguides extending away from the vertical section 68, these waveguides eventually bend toward one another and are merged/joined with one another as they proceed farther away from the vertical section.

FIG. 4 in particular shows how four adjacent pairs of the eight waveguides of the array 74 bend and merge with one another to form an array of four waveguides 77. However, it should further be understood that FIG. 4 only shows the portion of the demultiplexer 76 in which eight waveguides are merged into four waveguides, and that the demultiplexer additionally involves the merging of those four waveguides into two waveguides and then subsequently into a single output waveguide. During operation of the device 60, the demultiplexer 76 receives time-multiplexed signals from eight detection zones corresponding to the eight waveguides of the array 74. As described in further detail below in relation to FIG. 7(*a*) et seq., through the use of the information obtained from the array 74, the 8×1 demultiplexer 76 is able to generate an overall signal that includes all of the information obtained from the eight detection waveguides, and to restore the time domain signal chain.

Although both the devices 40 and 60 of FIGS. 3(*a*)-(*b*) and 4 are capable of achieving enhanced detection sensitivity through the use of the multiple detection waveguides in their respective waveguide arrays 52, 54, 72 and 74, the use of the demultiplexer 76 in the device 60 makes it possible to reduce the number of detectors receiving the light communicated by way of the waveguides to only one detector (or at least to a number of detectors less than the number of waveguides that are interfacing the fluidic channel). Thus, use of the demultiplexer 76 allows for a savings of the hardware costs associated with having multiple detectors (albeit at an expense of device throughput).

The detection sensitivity achieved by the devices 40, 60 is dependent upon the number of detection waveguides of the arrays 52, 54, 72 and 74. This is true both whether the demultiplexer 76 is employed or not employed (where the demultiplexer is not employed, as discussed in further detail below, the multiple signals provided by the multiple waveguides of each array can be used to perform cross-correlation operations so as to achieve enhanced signal-to-noise ratios). Indeed, the detection sensitivity can be enhanced by increasing the number of waveguides of the array 74 and/or the space-demultiplexed waveguide structure. Nevertheless, in the present embodiments of FIGS. 3(*a*)-(*b*) and 4, with a total of eight waveguide detection channels/zones, the detection sensitivity can be enhanced by nearly 1,000 times in comparison with that afforded by a single channel device. This manifests one advantage of the FPIC approach over free-space optical set-ups used in performing conventional flow cytometry because for the latter, the number of interrogation zones is significantly limited by space and cost.

Figure 5A:
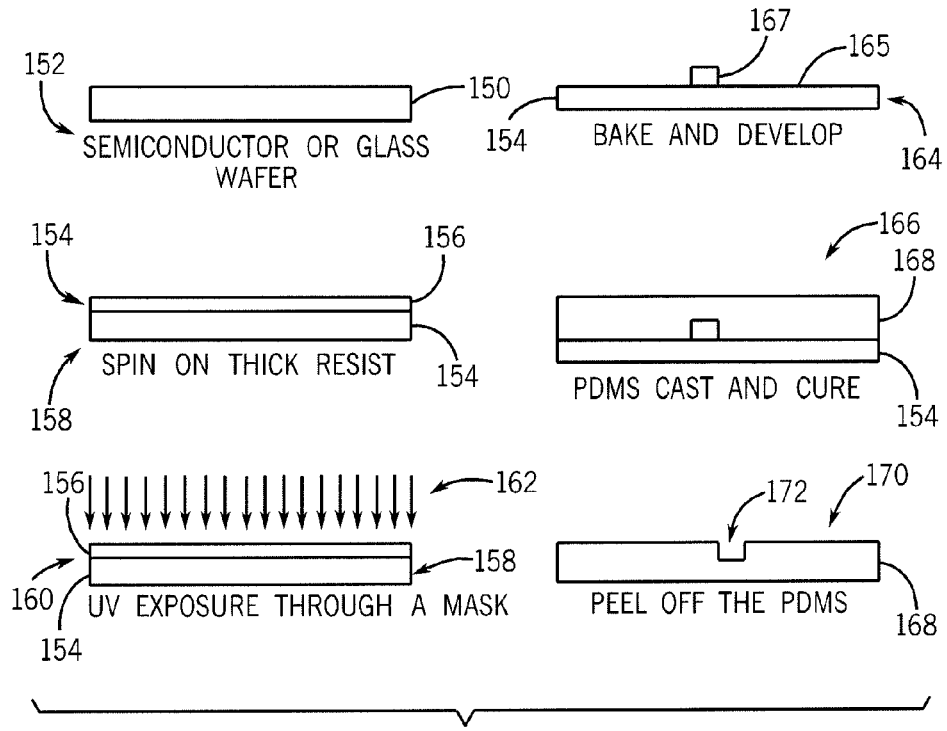
FIGS. 5(a)-(b) show steps of an exemplary process that can be employed to fabricate one or more fluidic channels employed in the devices of FIGS. 3(a)-(b) and 4.
Figure 5B:
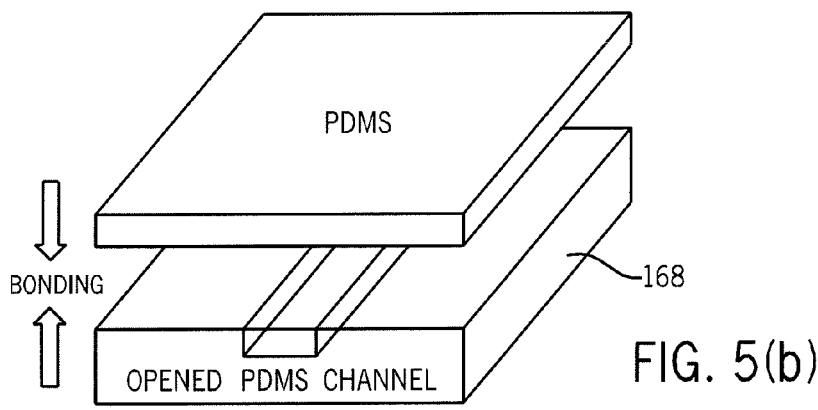

The fluidic-photonic integrated circuit (FPIC) devices 40, 60 in the embodiments of FIGS. 3(*a*)-(*b*) and 4 are made entirely (or substantially) of polymer such as PDMS, and are fabricated by way of micro-molding and waveguide capillary filling. Details of the micro-molding process that can be utilized to create the devices 40, 60 of FIGS. 3(*a*)-(*b*) and 4 are illustrated in FIG. 5(*a*)-(*b*). As shown in FIG. 5(*a*), a soft lithography process can be employed to fabricate microfluidic channels such as the channels 50, 70 discussed above. As shown, a semiconductor or glass wafer 150 is provided at a step 152, and then at a step 154 a spin-on thick resist 156 is added to the wafer to form a combined structure 158. Further, at a step 160, the combined structure is exposed to ultraviolet light 162 by way of a mask (not shown). Subsequent to the photo-lithographic patterning step 160, the combined structure 158 is now a modified combined structure 165 having a modified (patterned) thick resist layer 167. The modified combined structure 165 can also be referred to as a "mold master".

Subsequent to the step 160, the modified combined structure 165 is then baked by way of a thermo-curing process, for example, thermo-curing at 65° C. for 4 hours. Then, at a step 166, a pre-polymer layer 168 is cast and cured upon the modified combined structure 165. Then, at a step 170, the pre-polymer layer 168 is peeled from the mold master, thus transferring the pattern to the pre-polymer layer. In at least some embodiments, the mold master is made from photo-lithographically patterned SU-8-50 photoresist (such as that available from MicroChem, Inc. of Newton, Mass.) on a 4" silicon wafer (such as that available from Silicon Quest International, Inc. of Santa Clara, Calif.). Also, the pre-polymer layer 168 cast onto the mold master can be a PDMS layer such as Gelest OE 41 available from Gelest, Inc. of Morrisville, Pa.

The steps shown in FIG. 5(*a*) result in the creation of the pre-polymer (PDMS) layer 168 that has channel patterns 172 complementary to the patterns of the modified thick resist layer 167. Referring additionally to FIG. 5(*b*), in order to make an enclosed microfluidic channel, the pre-polymer layer 168 is in turn bonded to another pre-polymer (e.g., PDMS) layer 174. Typically, both of the pre-polymer layer 168 and 174 will have the same refractive index (e.g., 1.407). A short treatment (e.g., 10 seconds) of high power (e.g., 100 Watts) oxygen plasma (e.g., using the Technics 500-II Plasma Etcher and Asher System) can be used to activate the surfaces of the pre-polymer layers 168, 174 to facilitate permanent bonding of those layers, thus completing the fabrication of one or more microfluidic channels corresponding to the patterns 172. In alternate embodiments an ultraviolet/ozone treatment can be employed instead of the oxygen plasma treatment to achieve bonding.

Various similar molding techniques can also be used to fabricate ridge waveguides with a chosen polymer of an appropriate refractive index, which can be employed as the waveguides 42, 44, 62, 64 or the waveguides of the waveguide arrays 52, 54, 72 and 74 described above. One such technique that can be employed to make the waveguides is a channel-waveguide filling process. To make channel waveguides by way of this technique, some chosen channels are filled with a polymer of higher refractive index, for example, Gelest OE 42 PDMS (also available from Gelest Inc.) can be chosen as the core material. Pre-polymer is introduced into the channels through the inlets. Pre-polymer can completely fill the channels in a short period of time, e.g., 20 minutes. Then, upon performing the same thermo-curing procedure as mentioned before, the core material is solidified and takes on a desired refractive index (e.g., 1.42). It should be further noted that, if striations at the end of a waveguide are caused due to waveguide cutting, these can be removed by polishing; at the same time, facet polishing does not appear to be usually necessary since the striations have not appeared to disturb experimental signal measurements.

For the purpose of realizing monolithic fluidic-photonic integrated circuits (FPICs), several integration schemes can be utilized. For example, for high sensitivity chemical sensors that require long interaction length, one can employ an integrated structure having a single-mode ridge waveguide inside or aligned with the microfluidic channel so that the light wave propagates in the same direction as the flow. More particularly, to achieve such an integrated structure, both the waveguide and the microfluidic channel are formed in the same fabrication process, with the waveguide being formed by creating passage(s) with walls of a first, lower index of refraction that are subsequently filled with a liquid that, upon being solidified by heat or UV treatment, takes on a second, higher index of refraction. The microfluidic channel can have the same cross-sectional dimensions as the waveguide, or the two structures can have different cross-sectional dimensions, as desired. Also, for applications where on-chip optical processing or contact-free detection is needed, one can also employ a stacking structure in which waveguides and fluidic channels are located at different planes so that the waveguides and fluidic channels can be routed without crossing one another.

Still another manner of integrating waveguides and fluidic channels is a self-forming technique that utilizes a capillary effect and immiscibility between liquids inside microfluidic channels to create waveguides that intersect the microfluidic channels. Such an integration scheme is particularly suitable for highly-localized fluorescent excitation and detection. For the self-forming process, a fluidic channel and a waveguide channel (or multiple waveguide channels) are formed that intersect with one another. The fluidic channel is then filled up with BSA (protein) aqueous solution before liquid (pre-polymerized) PDMS is provided to fill the waveguide channel(s) that intersect the fluidic channel. Since the liquid PDMS and the BSA solution are immiscible, the liquid PDMS will not enter the fluidic channels even though they intersect. After the liquid PDMS is thermally (e.g., at 60 degrees C.) or UV cured to become solid PDMS, the BSA solution is removed from the fluidic channel, yielding an array of waveguides in very close proximity to the fluidic channels for efficient light coupling. In at least some embodiments of FPICs to be used for flow cytometry, a waveguide/channel integration structure similar to but simpler than what is used in the self-forming technique can also be employed.

Notwithstanding the above discussion, the present invention is intended to encompass a variety of FPIC devices having features, or being fabricated by way of techniques, other than those mentioned above. For example, in alternate embodiments, FPIC devices can have any number of detection waveguides corresponding to the arrays of waveguides 52, 54, 72 and 74, including more than eight or less than eight waveguides in each array (or even only one waveguide on each side of the fluidic channel). Likewise, although the waveguides of the arrays 52, 54, 72 and 74 are perpendicular to the vertical sections 48, 68 of the fluidic channels, in alternate embodiments, the waveguide(s) can approach the fluidic channels at oblique or other angles. Curved waveguide surfaces can also be formed to create light focusing effects to either increase the numerical aperture of the waveguides or to move the waveguides further away from the fluidic channels. It should further be noted that, while in at least some embodiments such as those discussed above, the FPIC devices are PDMS-based microchips, in alternate embodiments the FPIC devices can be made from other materials and via other processes than are used to develop PDMS-based microchips.

Figure 6:
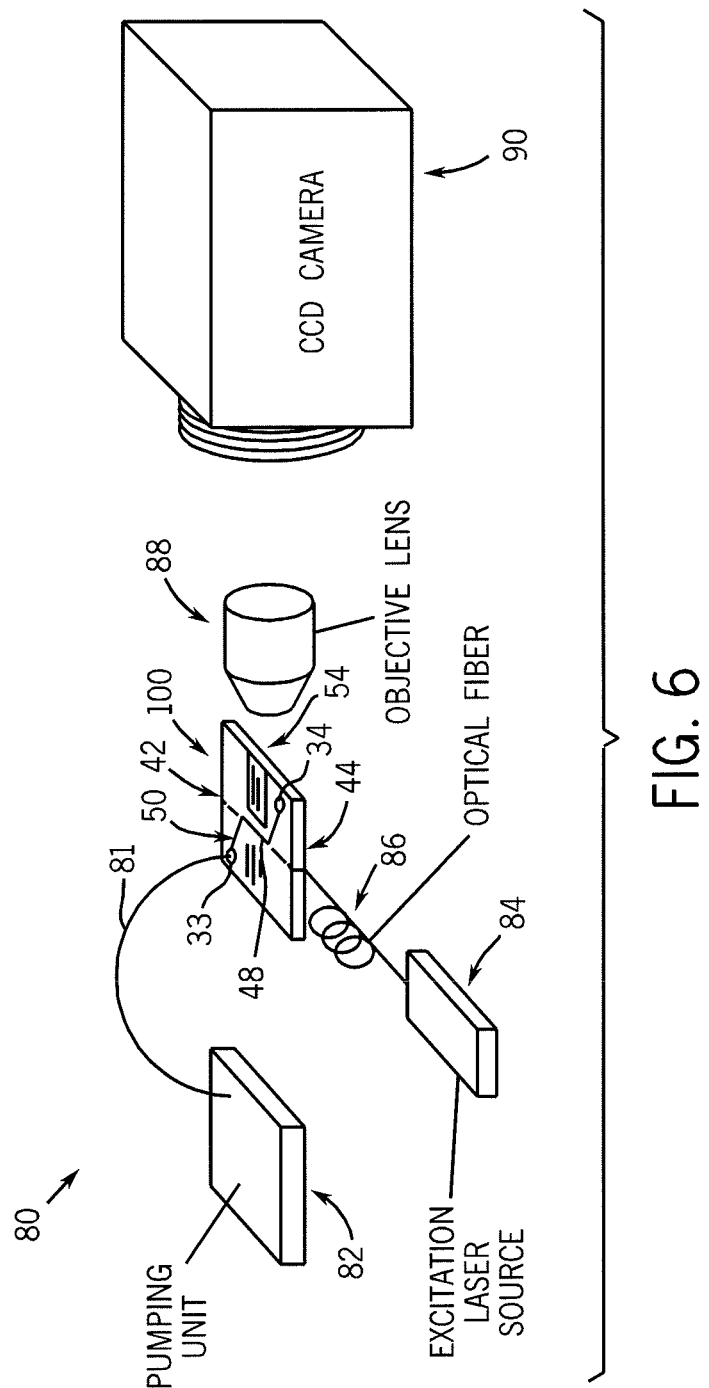
FIG. 6 shows in schematic form an improved optical detector in accordance with at least some embodiments of the present invention, where the detector employs a fluidic-photonic integrated circuit similar to that of FIGS. 3(a)-(b)

Referring to FIG. 6, an exemplary flow cytometry system 80 employing a FPIC device 100 similar to the device 40 of FIGS. 3(a)-(b) (e.g., without any demultiplexer) is shown in schematic form. As shown, the FPIC device 100 includes the microfluidic channel 50 having the vertical section 48 and the first and second inlet/outlets 33, 34, as well as the excitation waveguides 42 and 44. However, in this embodiment (contrary to that of FIGS. 3(a)-(b)), only one of the waveguide arrays 52, 54 (namely, the right-side array 54) is employed and, as a result, signals are only detected along one side of the microfluidic channel 50. Further as shown, the first inlet/outlet 33 functions as an inlet and receives pumped fluid from plastic tubing 81, by which the inlet is coupled to a pumping unit 82. The second inlet/outlet 34 in turn functions as an outlet that in the present schematic diagram is shown to be left open but which typically is coupled to a receptical such as a waste beaker (e.g., in an experimental set-up) or can be coupled back to the pumping unit 82. As part of the standard microfluidic device fabrication and packaging process, appropriate connectors can be fabricated to connect the plastic tubing 81 to the inlet 33 on the chip without leakage. In at least some embodiments, a syringe pump can be used as the pumping unit 82 to deliver liquid samples.

Also, in the present embodiment, laser excitation light from a source 84 is coupled by way of multi-mode optical fiber 86 to one of the two waveguides 42, 44 (in this case the waveguide 44) that are aligned with and face the respective ends of the vertical section 48 of the fluidic channel 50. In the present embodiment, to secure the connection between the optical fiber 86 and the waveguide 44, a multi-mode fiber is inserted into the waveguide channel prior to filling of that channel with pre-polymerized PDMS and solidification of that PDMS (before the core material of the waveguide is solidified) such that, after PDMS curing and solidification, an encapsulated fiber-waveguide structure is created. Such an encapsulated fiber-waveguide structure is capable of showing low insertion loss (<0.3 dB) and negligible interface reflection, as well as mechanical robustness. Further as shown in FIG. 6, the light transmitted by the detection waveguides of the array 54 away from the fluidic channel 50 is directed toward an objective lens 88, which in turn provides that light to a CCD camera 90. A near-field image thus is formed on a CCD camera screen of the camera 90.

Depending the upon the embodiment, the camera 90 or another device in communication with the camera (not shown) can include a processing devices that receive signals from the camera, allowing for further processing operations to be performed, some of which are described in further detail below. The processing can be, for example, a microprocessor, programmable logic device or integrated circuit device such as a digital signal processing (DSP) chip or other processing device. In at least some embodiments, the processing device can be part of, or assume the role of, a control device or controller capable not only of processing information but also capable of generating and controlling the output of (e.g., on a display or onto a network, such as the internet) signals, information, or data. In some such embodiments, the controller also is capable of monitoring and/or controlling other devices/components of the flow cytometry system 80 such as the pumping unit, the excitation laser, and/or other devices/components. Further, in still other embodiments, a processing device and/or controller can be coupled to receive information from the detection waveguides via a device other than the camera 90. It should further be understood that embodiments of the invention not being employed for the purpose of flow cytometry also can employ a processing device or controller similar to that described above. Additionally, it should be understood that the processing device/controller should be generally understood to encompass one or more memory devices or computer-readable storage media capable of governing operation of the processing device/controller.

Figure 7A:
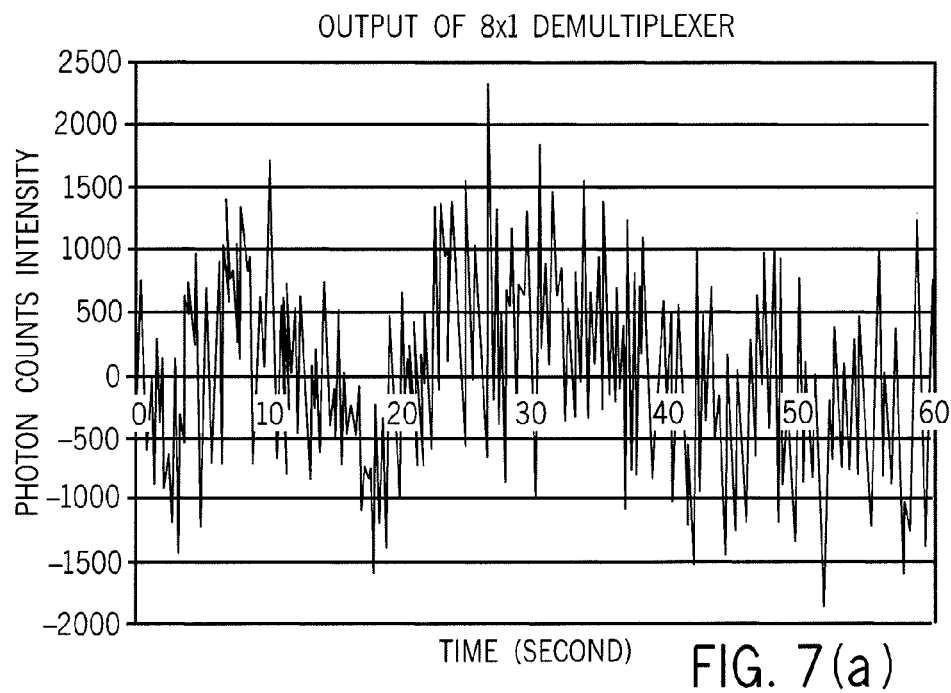
FIGS. 7(a) and (b) are graphs showing exemplary output signals from a single output of the waveguide demultiplexer of the fluidic-photonic integrated circuit of FIGS. 4(a)-(b)
Figure 7B:
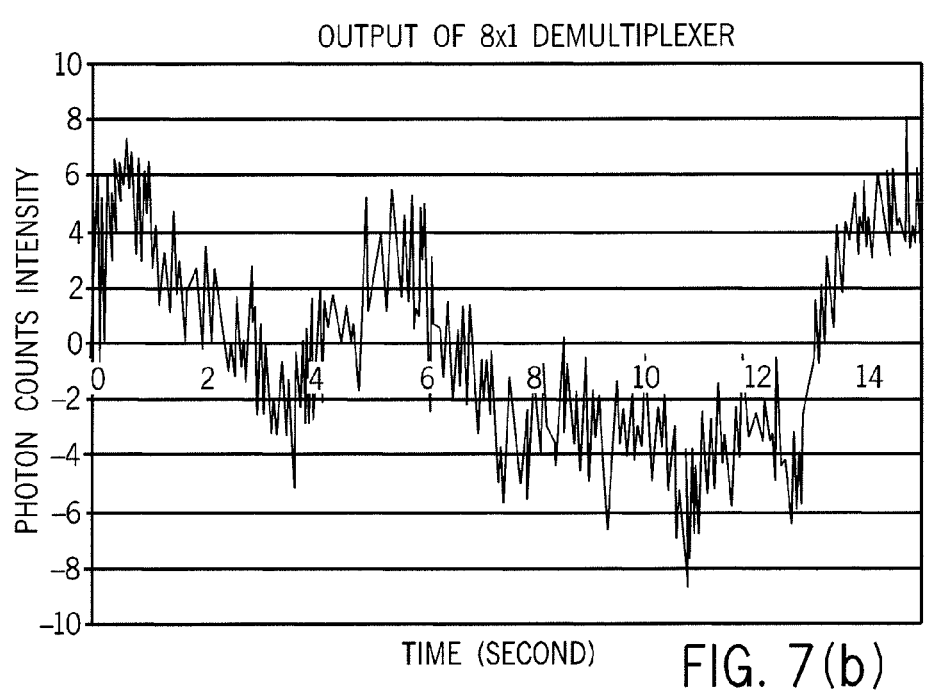

Although not shown in FIG. 6, a demultiplexer such as the demultiplexer 76 can also be employed as part of (or in conjunction with) the array of waveguides 54. As mentioned above, the 8×1 demultiplexer 76 of FIG. 4 serves to reduce the number of optical detectors needed to receive the light from the array of waveguides 74. Also, the demultiplexer 76 allows for the restoring of a time-domain signal chain from noise-masked data. Referring to FIGS. 7(a)-(b), exemplary output of a 8×1 demultiplexer such as the demultiplexer 76 of FIG. 4 in response to detected signals is provided to illustrate such operation of the demultiplexer. FIG. 7(a) in particular shows data that was obtained using a sample containing 5 μm fluorescent microbeads, while FIG. 7(b) in particular shows data that was obtained using a sample containing 1 μm fluorescent microbeads. The data represents the combination of the signals from 8 separate channels (e.g., the combination of all of the eight waveguides of the array 74).

When the detected output signal is weak, the raw data shown in FIGS. 7(a) and (b) can be largely corrupted by noise due to stray light and the electronic noise of the CCD camera. Nevertheless, in spite of the potentially poor signal quality, it is possible to perform the following algorithm to restore the signal chain in the time domain, utilizing the property that the signals detected at the eight sequential detection zones provided by the eight waveguides of the array 74 are time-correlated. Specifically, $$S(t)=f_1(t)*f_2(-T)*f_3(t-2T)*f_4(t-3T)*f_5(t-4T)*f_6(t-5T)*f_7(t-6T)*f_8(t-7T) \quad (1)$$

where S(t) is the time-dependent signal and T is the time interval for a particle to pass through two adjacent waveguide channels (e.g., to pass from one of the waveguides 74 to a neighboring one of the waveguides 74). The value of T can be obtained from the time-of-flight measurement.

Thus, using Equation (1), the time dependent signal S(t) is determined based on a concept of time-correlation among the detection waveguides, as represented by multiple signals $f_i(t)$. Additionally, it should be noted that, to remove the effects of high background and baseline drift, it is advisable to have each signal $f_i(t)$ be passed through a high-pass filter before performing the operation according to Equation (1). Further, since all of the various $f_i(t)$ signals represent signal intensity, negative values will be removed. For instance, should $f_1$ happens to show a negative value at a certain time "t", then the signal S(t) at the time t will become the product of the remaining 7 terms and its final value will be normalized by the power of 8/7. In other words, the normalized signal in the above case at the particular time becomes $S^{8/7}$.

Figure 8A:
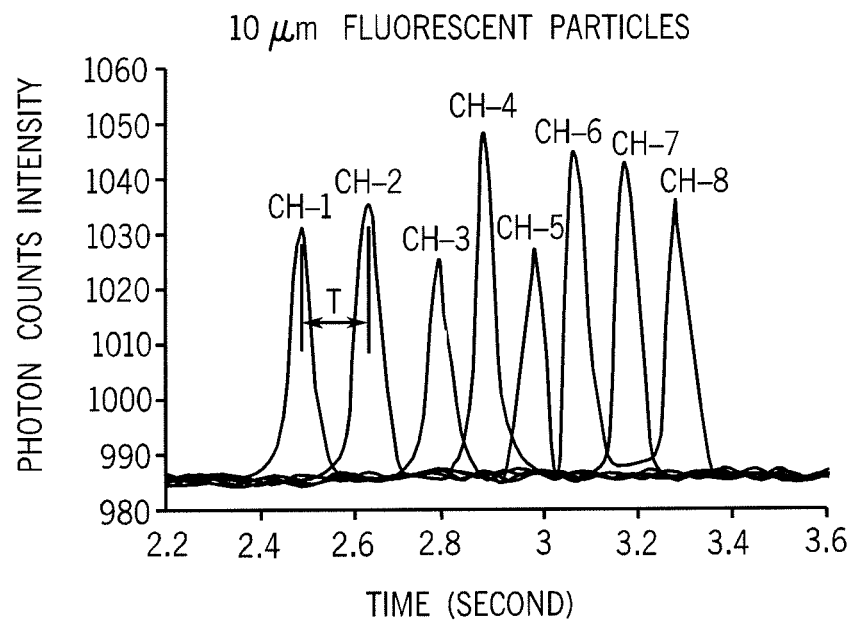
FIGS. 8(a)-(c) are graphs showing exemplary time variation of photon counts intensity generated from eight waveguide outputs of an alternate embodiment of the fluidic-photonic integrated circuit of FIG. 4 where the data in (a-c) were obtained from fluorescent beads of decreasing size and fluorescence intensity.

Turning to FIG. 8(a), as mentioned above, the arrays of eight parallel waveguides such as the array 54 of FIGS. 3(a)-(b) also can be used to perform time-of-flight measurements. More particularly, when a bead travels through the interrogation region (e.g., within the vertical section 48 of FIG. 4), its fluorescence is detected by each of the eight waveguides of the array 54 sequentially. The output intensity of each of the eight waveguides is recorded by the CCD camera 90. FIG. 8(a) shows exemplary intensities of the signals provided by the eight waveguide channels as functions of time, which were obtained using an experimental set-up employing 10 μm-diameter fluorescent beads. The center-to-center difference between intensity peaks (T) is the time period when a bead particle travels across two adjacent waveguides. Knowing the distance between the centers of adjacent waveguides of the array 54, the velocity of the bead particle can be easily obtained. It should be further noted that, in the case of 10 μm fluorescent beads, images of high signal-to-noise ratio can be obtained directly from the output of any single waveguide.

Figure 8B:
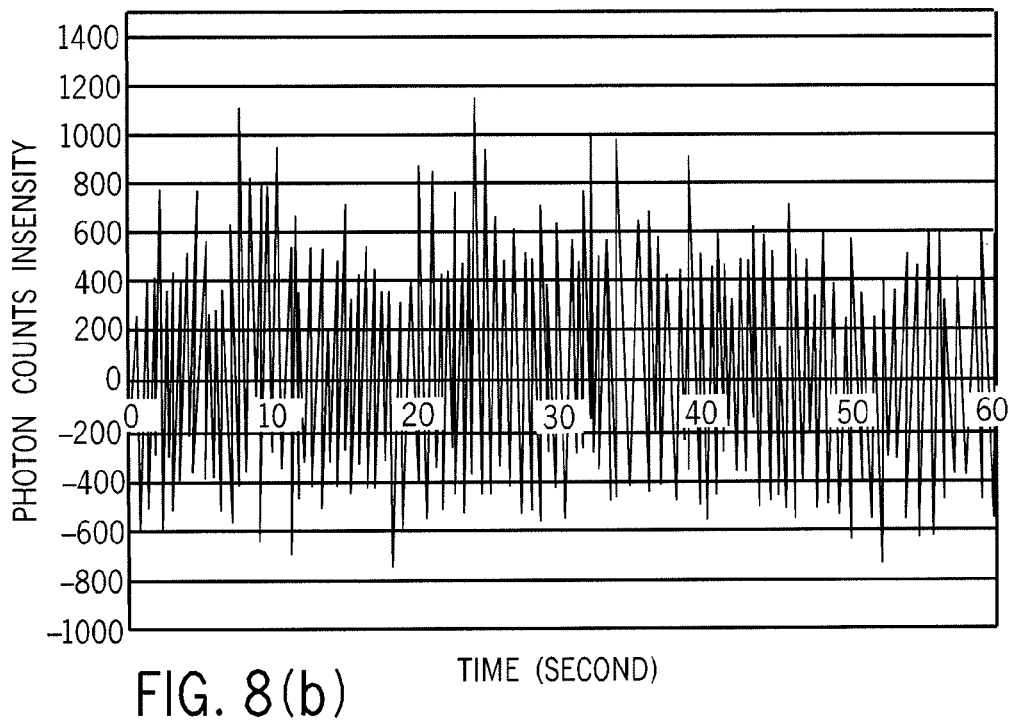
Figure 8C:
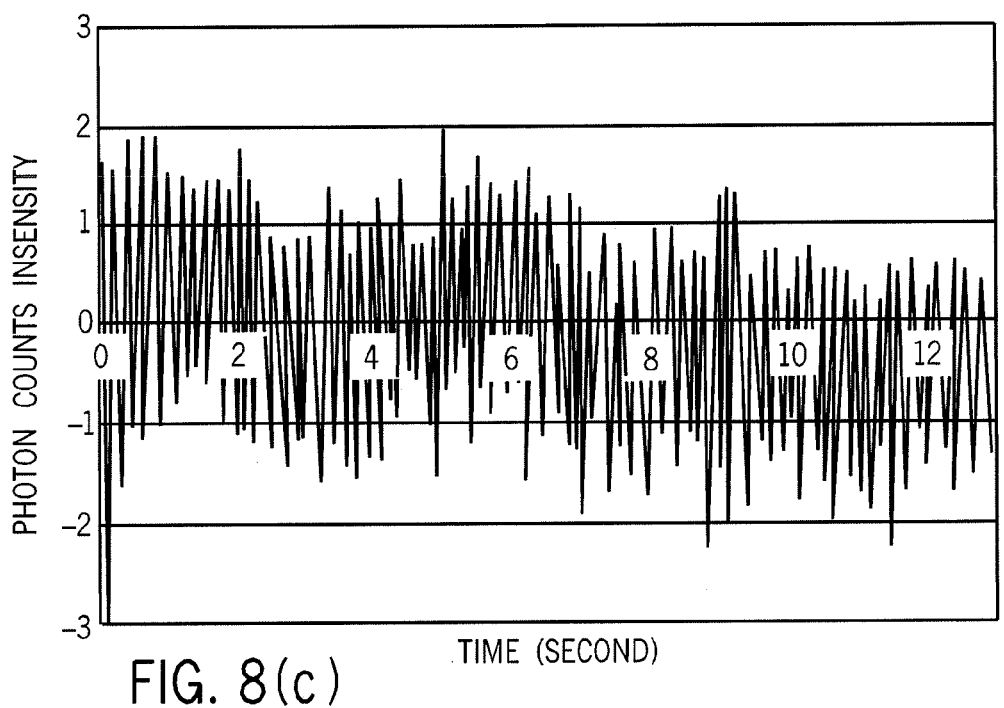

Referring to FIGS. 8(b)-(c), to demonstrate the ability of sensitivity enhancement with the array waveguide structure, exemplary time-of-flight measurements were also performed using fluorescent beads of smaller diameters than the 10 μm beads that were the basis of FIG. 8(a), namely, 5 μm (FIG. 8(b)) and 1 μm (FIG. 8(c)). Because these fluorescent microbeads have fluorescent dye doped over their entire volumes, the fluorescent intensity of each respective bead is proportional its volume, making the fluorescence intensity eight times and one-thousand times weaker than that of the 10 μm beads. FIGS. 8(b) and 8(c) respectively demonstrate that the directly-detected signals at the output of each waveguide channel resulting from the 5 μm beads and 1 μm beads, respectively, can be obscured and masked by the noise. Such output from any single channel, analogous to the signal obtained from a conventional flow cytometer using a low power excitation source and a low sensitivity detector, cannot produce any meaningful signal (it is for that reason that conventional flow cytometry systems require high power lasers and photomultiplier tubes with photon counting sensitivity, which are expensive and non-scalable in size).

FIGS. 8(b)-(c) demonstrate that it can become more difficult to achieve desired signal-to-noise ratios as the particles to be sensed become smaller. In these circumstances, the methodology described above with respect to Equation (1) for restoring a signal from noisy measurements may be inadequate for achieving output signals having desired signal-to-noise ratios. In particular, although Equation (1) provides a method that is mathematically simple, a more robust method to restore the real signal produced by each passing particle/analyte may be useful. In accordance with additional embodiments of the present invention, one such more robust method for providing output having improved signal-to-noise ratios is an additional multi-channel detection technique that involves cross-correlation analysis. This calculation assumes that signals are correlated to beat between the different waveguides of a waveguide array such as the array 54, and takes advantage of the knowledge that the true (light output) signals are time-correlated while the noise is not.

Figure 9:
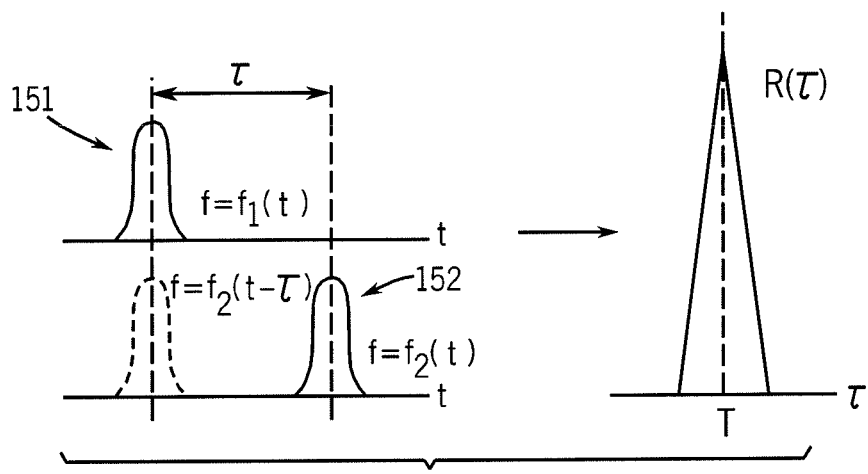
FIG. 9 is a schematic illustration of time domain cross-correlation.

The concept of cross-correlation is further illustrated graphically in FIG. 9. As illustrated, when a given particle passes through the vertical section 68 of the fluidic channel 50, first and second signals 151 and 152 will be generated at two of the neighboring detection waveguides of the array 54. As long as the signals 151, 152 from the two channels are time correlated, it is possible to obtain the time delay τ between the two signals by calculating a cross-correlation function R(τ) defined in Equation (2):

$$R(\tau) = \int f_1(t) * f_2(t-\tau) dt \qquad (2)$$

where $f1$ and $f2$ are normalized intensity functions of two individual channels and τ is a time domain variable. The cross-correlation function R(τ) (also shown in FIG. 9) that maximizes τ becomes equal to the time-delay between the two signals.

The above-described cross-correlation function can be extended for implementation in relation to an array having an arbitrary number of detection waveguides. For example, with respect to the FPIC device 100 in the above-described embodiment of FIG. 6 that has eight waveguide channels, the above analysis can be extended to calculate an eight-channel cross-correlation, as follows:

$$R(\tau) = \int f_1(t) f_2(t-\tau) f_3(t-2\tau) f_4(t-3\tau) f_5(t-4\tau) \\ f_6(t-5\tau) f_7(t-6\tau) f_8(t-7\tau) dt \qquad (3)$$

In comparison with Equation (2) with its two terms, this eight-term multiplication further serves to amplify the signal and suppress the noise. It should further be noted that, with respect to Equations (2) and (3), it is not necessary to assume that every particle/analyte travel at exactly the same speed as is assumed in Equation (1), since the application of Equations (2) and (3) involves the calculating of the travel velocity and time delay of each passing particle/analyte.

In view of the above considerations, use of an FPIC device/system (and especially a microfluidic FPIC) such as the FPIC device 100 and system 80 of FIG. 6 can be particularly advantageous when implemented in conjunction with cross-calculation techniques. Although the cross-correlation calculations according to Equations (2) and (3) are more computation heavy than those according to Equation (1), the calculations according to Equations (2) and (3) alleviate the requirement for keeping all of the particles/analytes in the streamline of a constant velocity, thus greatly simplifying the design and processing complexities of fluidic channels. Further, because the FPIC devices can accommodate essentially any number of detection waveguide channels without increasing the cost and complexity of the system substantially, the advantages in signal quality achievable using the cross-calculation techniques are fully realizable.

Figure 10:
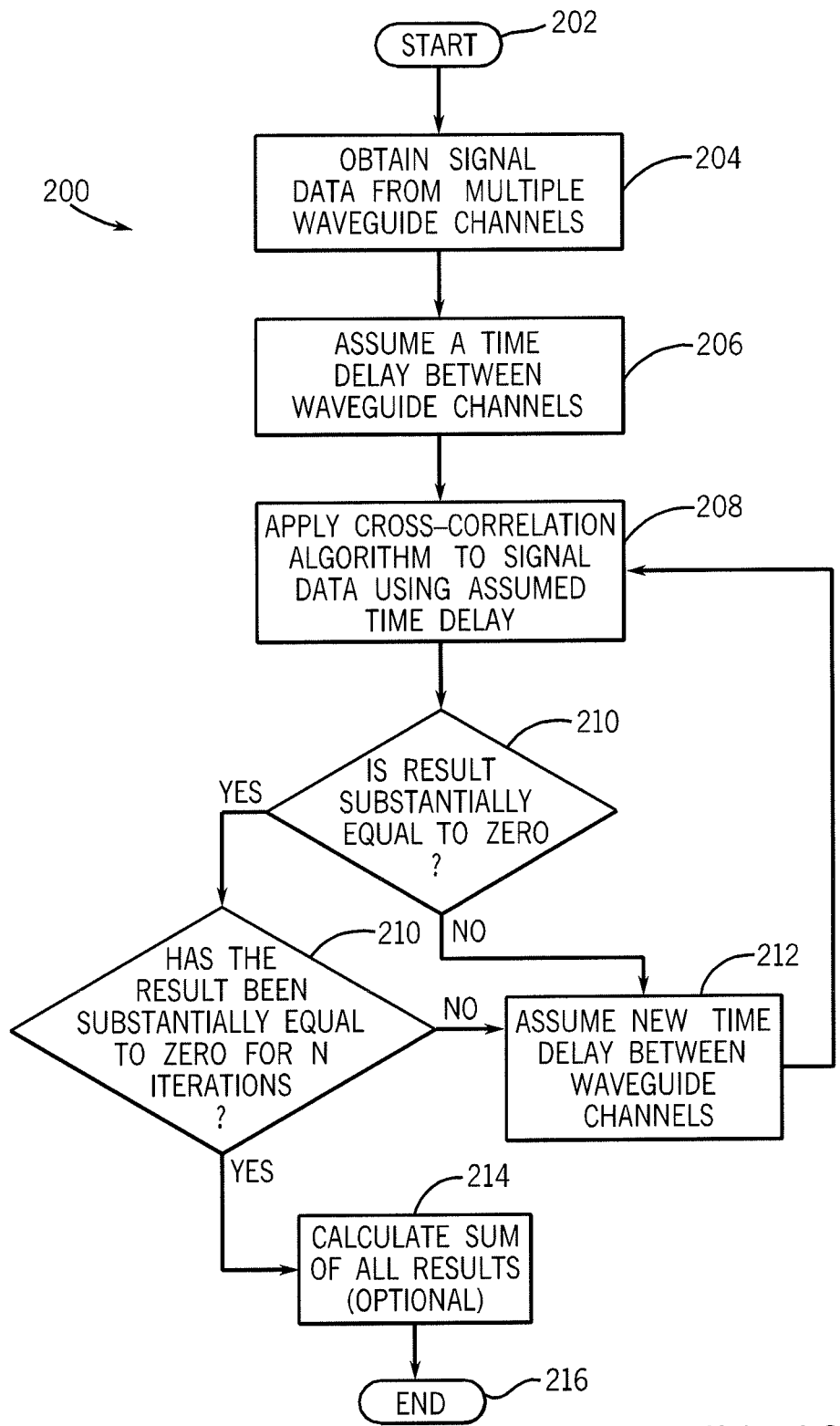
FIG. 10 is a flow chart illustrating steps of an exemplary iterative cross-correlation process.

Additionally, although the cross-correlation calculations according to Equations (2) and (3) when performed in the manner described above can be relatively computation intensive, a further time domain spectroscopy detection process shown by a flow chart 200 in FIG. 10 can reduce the computational intensity of cross-correlation. In particular, as shown in the flow chart 10, upon starting the flow chart at a step 202, the process begins at a step 204 by obtaining the signal information from the waveguides of the waveguide array (e.g., by way of a CCD camera receiving signals from the waveguides of the array 54 of FIG. 6). Then, rather than calculating the time delay τ associated with the movement of particles between neighboring waveguides of the waveguide array, at a step 206 a value for the time delay is assumed. The time delay τ in particular can be thought of as representing a range of times centered about a center time that is τ (e.g., τ=0.5 ms+/− 0.5 ms). Subsequently, at a step 208, the cross-correlation algorithm (e.g., Equation (3) for an eight-waveguide array) is applied to the signal information and, at a step 210, it is determined whether the result from performing this operation is zero (or substantially zero, e.g., negligible).

If the result is not zero (or substantially below a set threshold value), then at a step 212 a new value is assumed for the time delay, and step 208 is re-performed given that new value. The newly-assumed value of the time delay τ is typically an adjacent, incremental value relative to the previously-assumed value (e.g., given the first assumed value mentioned above, the next assumed value would be τ=1.5 ms+/−0.5 ms). Given that the step 212 cycles back to the step 208, the steps 208, 210 and 212 can be repeated iteratively as long as successive cross-correlation calculations produce non-zero results. However, once the result at step 210 is determined to be zero (or substantially zero), then it is further determined at a step 212 whether that has occurred already for a number of (e.g., N) iterations. If not, then the process again returns to step 212 at which another time delay is assumed, and further proceeds to repeat steps 208 and 210. However, if upon reaching step 212 it is determined that there have already been N zero results corresponding to N different time delay values, then the process diverts to a step 214 at which a sum of all of the different results corresponding to the different assumed time delay values is calculated, and subsequently to a step 216 at which the process ends. The step 214 is optional and, in some embodiments is not performed such that the process diverts directly to step 216 from step 210.

Due to the use of the assumed values of the time delay τ, the cross-correlation computation process of the flow chart 200 can be advantageous in comparison with the previously-described cross-correlation processes. In particular, by assuming the values of the time delay, computational effort need not be expended in determining the actual time delay value. Further, although numerous (e.g., fifty or more) iterations need to be performed in some circumstances to reach the criterion of the step 210 at which the iterations are stopped, this does not take excessive time since, given an appropriate digital signal processing (DSP) chip/device that performs time-shifting (e.g., any of several DSP chips available from Texas Instruments, Inc. of Dallas, Tex. that are capable of performing several hundred million instructions per section (MIPS)), the different iterative calculations can be performed simultaneously or nearly simultaneously in parallel. The speed at which the calculations are made in particular can surpass the flow rate of the particles/beads within the fluidic channel.

It should also be noted that the result obtained from applying the cross-correlation algorithm (e.g., Equation (3)) during each iteration at the step 208 is representative of the amount or number of particles flying by the waveguides of the waveguide array at a given speed corresponding to the assumed time delay, and thus the individual results are of individual interest as being representative of the amount of particles passing through the fluidic channel at different speeds. This can be valuable in the context of flow cytometry, particularly where it may be expected (or of interest) that different cells or different DNA base pairs travel at different speeds. At the same time, the sum of all of the individual results calculated optionally at the step 214 also can be of interest, as an indication of the total sample intensity.

Figure 11A:
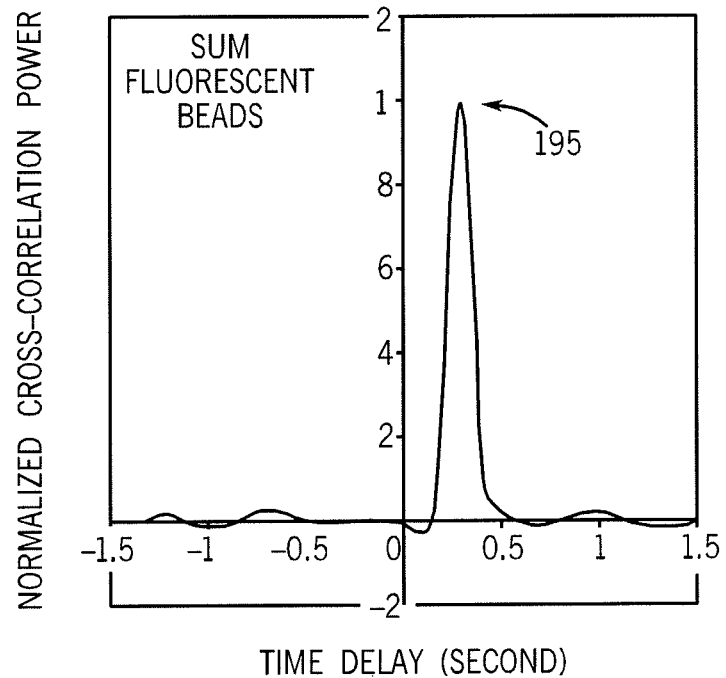
FIGS. 11(a) and (b), respectively, are graphs showing exemplary cross-correlated signals obtained using the raw data of FIGS. 8(b) and (c), respectively.
Figure 11B:
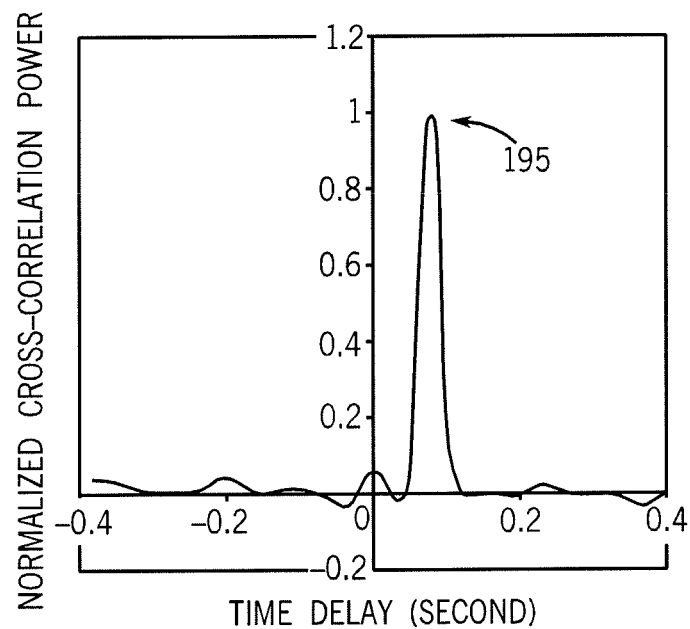

Referring additionally to FIGS. 11(a) and (b), these FIGS. provide an illustration of the effectiveness of the above-described cross-calculation techniques when implemented in relation to the system 80 of FIG. 6 with its FPIC device 100 having the array 54 of eight waveguides. More particularly, FIGS. 11(a) and (b) respectively illustrate exemplary cross-correlation data that can be obtained by applying Equation (3) to the raw data of FIGS. 8(b) and 8(c), respectively, with each of the FIGS. 11(a)-(b) displaying R(τ) as a function of τ. Clearly the signals have been completely restored as manifested by pronounced peaks 195 of R(τ) shown in each case. As shown, the maximum of R(τ) occurs at 0.3 sec and 0.08 sec for the two cases involving 5 µm and 1 µm beads, respectively.

These are the durations required for the respective particles to travel across two neighboring waveguide channels of the array of waveguides. For a center-to-center channel spacing of 100 µm, the velocities of particles in each case are 334 m/sec and 1250 µm/sec respectively. Therefore, the eight-channel waveguide array shows its superb ability of signal enhancement to allow for time-of-flight measurement on even extremely weak fluorescent beads. The velocity obtained in this way is a direct measurement of particle speed and can be used for in-situ calibration of the fluidic system.

Figure 12A:
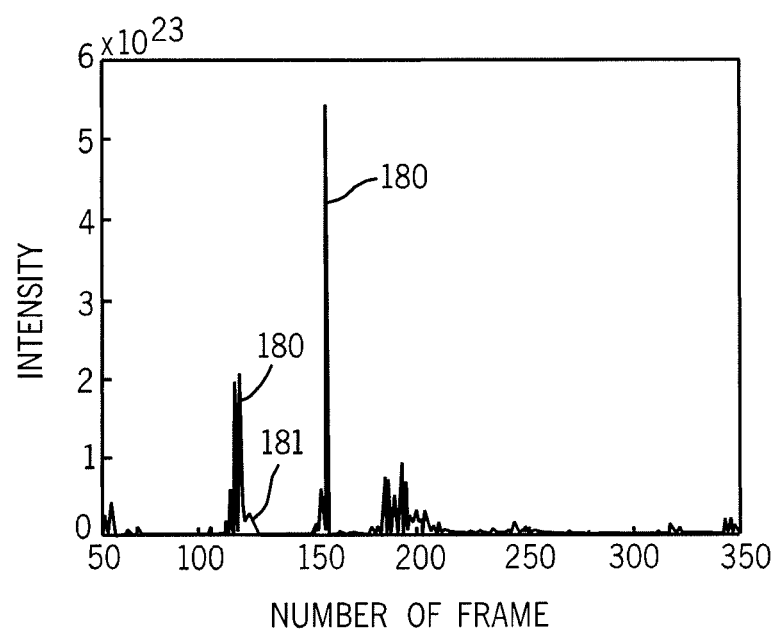
FIGS. 12(a) and (b), respectively, are graphs showing exemplary signal chains obtained using the raw data of FIGS. 7(a) and (b), respectively.
Figure 12B:
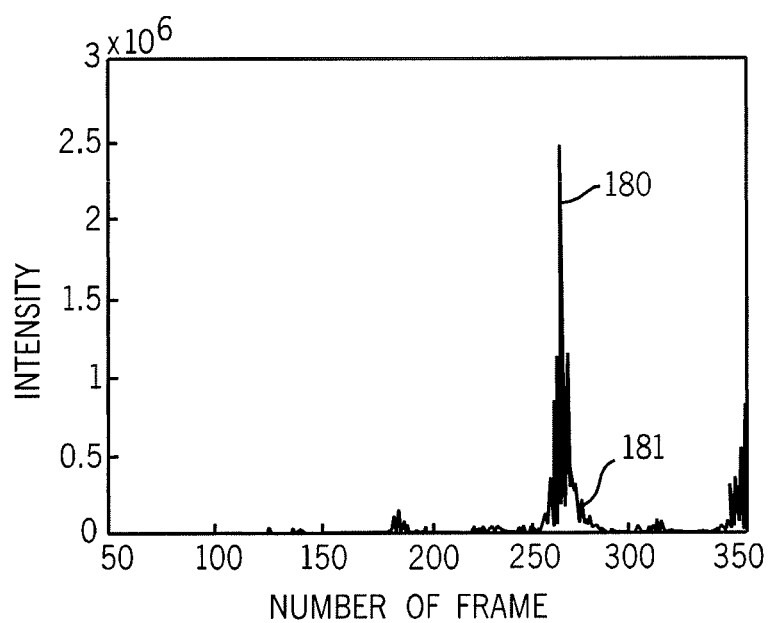

Turning to FIGS. 12(a)-(b), for particle detection and sorting, it is further desirable to measure signals in real time as an intensity signal chain. To generate the signals shown in FIGS. 12(a)-(b), the noise-masked raw data in FIGS. 7(a)-(b) obtained using the output of the 8×1 demultiplexer 76 and pertaining to the 5 µm and 1 µm bead data, respectively, is processed through Equation (1), with the value of T obtained from the previous time-of-flight measurement. Distinctive peaks (e.g., groups of spikes) 180 with side-lobes 181 represent passing beads in real time. From the results in FIGS. 12(a)-(b), it is evident that the values of the peaks 180 of the 5 µm beads are many (e.g., 17) orders of magnitude greater than those of 1 µm beads, which is due to the fact that Equation (1) is a product of eight correlated signals and therefore significantly magnifies the difference in signal intensity. These results suggest that the scheme of multi-channel detection not only improves the signal-to-noise ratio but also enhances the ability to distinguish signals of slightly different intensity, which is an important capability in the context of flow cytometry. (It should be noted that, in FIGS. 12(a)-(b), intensity can be of any arbitrary unit, and the dimension "number of frame" corresponds to time with, more particularly, one frame corresponding to 1/30 second.)

It should further be noted that, for detection and sorting in some conventional flow cytometry systems, emission intensity is used to identify targets of different characteristics. Although cell sorting by intensity is the predominant and simplest method, it is not as reliable and accurate as desired when the intensity difference between normal and targeted samples is small. As shown in FIGS. 12(a)-(b), the peaks produced by passing beads show considerable differences in their magnitude even though these beads belong to the same group within a variation of a few percents in their size and shape. Variations in the values of the peaks 180 can be partly attributed to non-uniformity of the beads. These large intensity variations of these "similar" beads suggest the ability of detection schemes in accordance with at least some embodiments of the present invention to distinguish samples of only small difference, thus making cell detection/sorting by intensity more reliable and accurate.

In at least some further embodiments, it is desirable that compensation be provided to account for variation in the distance of a given bead passing each waveguide, which otherwise can cause signal intensity change due to the variation of light coupling efficiency. In some such embodiments, optical detection from the opposite side of the fluidic channel can be utilized to eliminate the effects of positional variation, since any positional variation of a bead is supposed to produce an anti-correlation signal between the oppositely-located waveguides. For example, using a FPIC device similar to the FPIC device 40 having the arrays 52 and 54, signals provided by the waveguides of the array 52 would compensate for the signals provided by the waveguides of the array 54. If a bead is away from the center of the fluidic channel, then the signal intensity from the waveguides near the bead (for example, the waveguides of the array 52) increases and the signal intensity from the waveguides farther from the bead (for example, the waveguides of the array 54) decreases. This yields a negative correlation between the output signals from the waveguides on both sides of the channel. At the same time, intrinsic property variations of the bead will produce a positive signal correlation. That is, when a bead has a low fluorescence efficiency, output signals from the waveguides on both sides are reduced. In addition, it should also be mentioned that improving the flow channel design such as using multiple stream laminar flows can also suppress the undesirable effects of positional variation.

Another noticeable feature for the signal peaks 180 in FIGS. 12(a)-(b) is the occurrence of the side-lobes 181. In an ideal case when the background noise is small, high main-lobe-to-side-lobe ratios should be obtained due to the algorithm of Equation (1). However, when the signal of each waveguide channel is comparable to the noise, the nonzero background potentially raises the magnitude of the side-lobes, which can become problematic particularly when the bead population increases sufficiently that the signals produced by neighboring beads interfere with each other through their side lobes. Nevertheless, it should be noted that the occurrence of side lobes or multiple peaks for a single passing bead is the result of using the simplest algorithm, namely, that of Equation (1). If Equation (3) is instead employed such that a sliding time scale is used to define the lower and upper limit of integration time interval, there will be no side lobes and the signal appears to be a sequence of peaks similar to those in FIGS. 11(a)-(b) in time domain. In that situation, the specific time for each peak represents the arrival time of the bead to the first waveguide. To avoid crosstalk, the flow rate should be controlled so that two beads are not passing the array at any given time (so as to set a limit of the device throughput for each fluidic channel, as well as possibly a system throughput, where the system throughput is the product of the throughput of each fluidic channel and the total number of channels).

In addition to the above-described embodiments, the present invention is intended to encompass a variety of other devices, systems and techniques/methodologies that include one or more of the above devices, systems and techniques/methodologies and/or portions thereof. For example, although not shown in the FIGS., in at least some additional embodiments, a CCD connected microscope can be placed on top of the sample device to simultaneously monitor the events happening in the fluidic channel in order to verify the counting accuracy. By comparing the monitoring video with the waveguide channel data obtained during the same period of time, it is possible to address the correspondence between individual beads and peaks.

Although such a methodology involving both the waveguide signals and monitoring video can be helpful, it is limited in two respects. First, the error rate determined by this methodology is only valid when the flow rate is slow, due to the restriction of the speed of the monitoring CCD. Further, the verified period of time can be limited, for example, because the image acquisition and process are executed by a personal computer. One way of achieving valuable data notwithstanding these restrictions is to incorporate real-time signal processing and sorting functions with the current detection architecture, so that targeted particles can be collected for counting and calibration. For example, to approach such a solution, it is possible to design and utilize signal processing circuits that will trigger the sorting mechanism in real-time when events are detected. Also, for the sorting part, a new sorting mechanism using acoustic waves can also be introduced. It is intended that, in at least some embodiments, a flow cytometer with complete functions of detection, signal processing and sorting will be integrated in a single chip platform.

Although not limited to applications relating to flow cytometry, at least some embodiments of the present invention can offer significant cost, size, and performance advantages that have a potential to improve or even revolutionize conventional flow cytometry techniques. The technology and the architecture design of FPICs in accordance with at least some embodiments of the present invention significantly enhance the detection sensitivity through multi-point detections, hence opening up the possibility of using low cost light sources (e.g., light-emitting diodes (LEDs) and lamps) and detectors (e.g., semiconductor avalanche photodiode detectors (APDs)) to replace mainframe lasers, photomultiplier tubes (PMTs), and lock-in amplifiers. It also offers new functions such as measurements of particle velocity, quantum efficiency fluctuation, signal difference between similar samples, etc. that could provide new insights in relation to biosensing. Additionally, the FPIC platform offers a natural path to form array structures for parallel processing, which makes up for the possible throughput reduction due to the lower flow rate of microfluidic circuits. As described above, FPIC devices can be made of polymer materials by way of simple yet controllable methods (e.g., micro-molding and capillary channel filling), and the devices can be readily transferred to semiconductor or silica substrates for integration with optoelectronic or electronic devices.

As discussed above, a significant purpose of at least some embodiments of the FPIC devices of the present invention when implemented for on-chip flow cytometry applications is to enhance the sensitivity of fluorescent detection using the architecture of array waveguides that provides multiple detection zones for objects traveling through the fluidic channel. In addition, the waveguide arrays can perform time-of-flight measurement and multi-label fluorescent detection with wavelength filters. Further, the monolithic integration of waveguides with microfluidic channels as described above is only one example of a variety of possible implementations of various structures on photonic ICs to realize flow-cytometry-on-a-chip and for other purposes. For example, fabrication methodologies such as those described above (or similar to those described above) can be employed to incorporate more functional optical waveguide devices, such as multiplexers/demultiplexers, power splitters, filters, polarizers, etc. to further enhance and expand the detection and analysis functions or for other purposes.

Although both the eight detector and single detector designs described above produce superior sensitivity in comparison with conventional optical detectors, designs such as that of FIG. 4 having an integrated demultiplexer are preferred in at least some circumstances, since in such designs only one detector rather than multiple detectors in the form of a detector array is required. Also, in embodiments where a semiconductor APD or a PMT is used, the detector bandwidth (e.g., >1 MHz) is more than sufficient to support the sampling rate (e.g., eight times of the particle throughput) for unequivocal detection of each passing particle, cell, bead, analyte, etc. In at least some embodiments, the use of an eight-channel waveguide array such as that mentioned above also allows for other measurements to be made that can yield useful information. These include, for example, time-of-flight measurements and timing jitter measurements to monitor Brownian motion and flow effects. Such information makes it possible to track the behavior of each individual particle in the fluidic channel, producing insight into the particle properties and signals for downstream control.

As mentioned above, the present invention is not limited to applications relating to flow cytometry but rather is intended to encompass a variety of embodiments of devices, systems and processes that can be utilized in a variety of biomedical, biochemical, and other sensing applications. Also, while in at least some embodiments of the present invention, one or more arrays of eight detection waveguides are arranged along one or more sides of a fluidic channel, in alternate embodiments, lesser or greater numbers of waveguides than eight waveguides can be employed (indeed, in at least some embodiments, only one detection waveguide is positioned along one or both sides of the fluidic channel). The waveguides can be oriented in a perpendicular manner relative to the fluidic channel as discussed above, but in alternate embodiments can be oriented in any particular manner relative to the fluidic channel. Also, while the FPIC devices shown in FIGS. 3(a)-(b), 4 and 6 employ waveguide arrays arranged on one or two opposing sides of the vertical sections 48, 68 of the fluidic channels 50, 70, in alternate embodiments it would further be possible employ two sets of waveguides that extended at right angles relative to one another (with the vertical sections serving as the vertex), or at other angles relative to one another rather than only at 180 degree angles relative to one another. Indeed, in further alternate embodiments, three, four or possibly even more arrays of waveguides can be positioned extending away from the vertical sections along three or more planes.

Additionally, while the detection waveguides can be square or rectangular in cross-section as shown, in alternate embodiments the waveguides can take on alternative cross-sectional shapes (e.g., circular cross-sections). Although the sections 48, 68 of the waveguides can be vertical as shown in FIGS. 4(a)-(b) and 5, the sections need not be vertical but rather can be horizontal or oriented in another manner and, in certain embodiments, can also be curved. Further, although the excitation waveguides 42, 44, 62 and 64 shown in FIGS. 3(a)-(b) and 4 are aligned with the vertical sections 48, 68, respectively of the fluidic channels, in alternate embodiments, any of a variety of other types of light sources (including simply light bulb(s)) could be utilized to illuminate the fluid flowing within the channels. In such other embodiments, it would not be necessary that the light be shined through/along the lengths of the fluidic channels as shown in FIGS. 3(a)-(b) and 4; indeed, in certain embodiments, the light can be directed toward the fluidic channels from any direction. Indeed, the present invention is intended to encompass embodiments of FPIC devices in which light (or other electromagnetic radiation) is detected via one or more waveguides or other conductive structures, but in which excitation light (or other electromagnetic radiation) is delivered to the fluidic channel by way of any of a variety of structures (including simply light bulbs), not merely by way of one or more waveguides.

Additionally, while the fluidic channels (e.g., the channels 50,70) of the devices described above are microfluidic channels, the present invention is further intended to encompass other embodiments of devices and systems that employ combinations of fluid channels and waveguides and/or electrodes even where the fluid channels are not "microfluidic channels". For example, the present invention is intended to encompass devices having fluid channels having dimensions substantially greater than those considered as being "microfluidic" channels, e.g., channels having cross-sectional dimensions of greater than micrometers or millimeters. Further, it is intended that the present invention encompass methods of constructing FPIC devices that involve conventional techniques for manufacturing microfluidic channels, and then supplement those conventional techniques with additional steps to integrate photonic components (e.g., waveguides) with those channels/carriers.

It is specifically intended that the present invention not be limited to the embodiments and illustrations contained herein, but include modified forms of those embodiments including portions of the embodiments and combinations of elements of different embodiments as come within the scope of the following claims.

What is claimed is:

1. A method of obtaining information regarding at least one particle suspended within a flowing fluid, the method comprising:
    applying light to the fluid and to the at least one particle suspended within the fluid as the fluid flows through a fluidic channel;
    obtaining scattered or fluorescent light resulting from an interaction between the light incident on the at least one particle and the at least one particle by way of a first plurality of optical channels extending away from the fluidic channel to at least one detection device;
    obtaining at least one signal at the at least one detection device based upon the scattered or fluorescent light; and
    performing a calculation based upon the at least one signal and one or more transit times required for the at least one particle to proceed between a neighboring pair of the first plurality of optical channels resulting in the information, the information being indicative of at least one characteristic of the at least one particle,
    wherein the first plurality of optical channels form an array of substantially-parallel optical channels having respective ends that are spaced apart from one another along the fluidic channel and wherein the optical channels merge with one another as they extend away from the fluidic channel, so that the scattered or fluorescent light propagating through the first plurality of optical channels is demultiplexed to arrive at a single, overall signal.

2. The method of claim 1, wherein the transit time is obtained using a second plurality of optical channels, the second plurality of optical channels forming an array of substantially-parallel channels having respective ends that are spaced apart from one another.

3. A method of obtaining information regarding at least one particle suspended within a flowing fluid, the method comprising:
    applying light to the fluid and to the at least one particle suspended within the fluid as the fluid flows through a fluidic channel;
    obtaining scattered or fluorescent light resulting from an interaction between the light incident on the at least one particle and the at least one particle by way of a first plurality of optical channels extending away from the fluidic channel to at least one detection device;
    obtaining at least one signal at the at least one detection device based upon the scattered or fluorescent light; and
    performing a calculation based upon the at least one signal and one or more transit times required for the at least one particle to proceed between a neighboring pair of the first plurality of optical channels resulting in the information, the information being indicative of at least one characteristic of the at least one particle,
    wherein the at least one signal includes a plurality of signals, and wherein the calculation comprises determining a product of a plurality of values corresponding respectively to the plurality of time-shifted signals.

4. The method of claim 3, wherein the plurality of time-shifted signals are shifted relative to one another by the one or more transit times.

5. A method of obtaining information regarding at least one particle suspended within a flowing fluid, the method comprising:
    applying light to the fluid and to the at least one particle suspended within the fluid as the fluid flows through a fluidic channel;
    obtaining scattered or fluorescent light resulting from an interaction between the light incident on the at least one particle and the at least one particle by way of a first plurality of optical channels extending away from the fluidic channel to at least one detection device;
    obtaining at least one signal at the at least one detection device based upon the scattered or fluorescent light; and
    performing a calculation based upon the at least one signal and one or more transit times required for the at least one particle to proceed between a neighboring pair of the first plurality of optical channels resulting in the information, the information being indicative of at least one characteristic of the at least one particle,
    wherein performing the calculation comprises iteratively performing two or more calculations based upon the at least one signal and the one or more transit times, wherein each additional iteration of the calculation results in a respective additional piece of information.

6. The method of claim 5, further comprising determining whether a threshold number of successive additional pieces of information have been determined to be substantially equal to zero and, if so, ceasing to perform the additional iterations.

7. The method of claim 5, further comprising calculating a sum of the information and the additional pieces of information, and outputting at least one of: the information, the sum, and derivative information based upon at least one of the information and the sum.

8. A method of obtaining information regarding at least one particle suspended within a flowing fluid, the method comprising:
    applying light to the fluid and to the at least one particle suspended within the fluid as the fluid flows through a fluidic channel;
    obtaining scattered or fluorescent light resulting from an interaction between the light incident on the at least one particle and the at least one particle by way of a first plurality of optical channels extending away from the fluidic channel to at least one detection device;
    obtaining at least one signal at the at least one detection device based upon the scattered or fluorescent light; and
    performing a calculation based upon the at least one signal and one or more transit times required for the at least one particle to proceed between a neighboring pair of the first plurality of optical channels resulting in the information, the information being indicative of at least one characteristic of the at least one particle,
    wherein performing the calculation comprises computing a product between a time-varying intensity function of the at least one signal and a time shifted version of the time-varying intensity function of the at least one signal.

9. The method of claim 1, wherein the one or more transit times are obtained prior to obtaining the at least one signal.

10. The method of claim 1, wherein the at least one particle has a diameter of approximately 1 micrometer.

11. The method of claim 1, wherein the at least one signal comprises two or more signals that are obtained from two or more detection devices configured to detect the scattered or fluorescent light from two or more of the first plurality of optical channels.

12. A method of obtaining information regarding at least one particle suspended within a flowing fluid, the method comprising:

applying light to the fluid and to the at least one particle suspended within the fluid as the fluid flows through a fluidic channel;

obtaining scattered or fluorescent light resulting from an interaction between the light incident on the at least one particle and the at least one particle by way of a first plurality of optical channels extending away from the fluidic channel to at least one detection device;

obtaining at least one signal at the at least one detection device based upon the scattered or fluorescent light; and performing a calculation based upon the at least one signal and one or more transit times required for the at least one particle to proceed between a neighboring pair of the first plurality of optical channels resulting in the information, the information being indicative of at least one characteristic of the at least one particle, wherein performing the calculation comprises:

(a) assuming a time value for each of the one or more transit times; and (b) performing a cross-correlation computation on the at least one signal based on the assumed time value(s);

(c) upon determination that the cross-correlation computation result is not below a threshold value, assuming a new time value for at least one of the one or more transit times and performing the cross-correlation computation based on the new assumed transit time value(s); and (d) upon determination that the cross-correlation computation result is below the threshold value, obtaining the information.

13. The method of claim 12, wherein the threshold value is zero.

14. The method of claim 12, wherein steps (a) through (c) are carried out iteratively for up to a maximum number of times.

15. The method of claim 12, wherein step (d) further comprises:

producing a count as to the number of times the cross-correlation computation result has remained below the threshold value; and obtaining the information if the count is greater than or equal to a predetermined count, obtaining the information.

16. The method of claim 12, wherein step (d) further comprises computing a sum of all cross-correlation results obtained in steps (c) and (d).

17. The method of claim 12, wherein the cross-correlation computation result is representative of number of particles that are suspended within the fluid as the fluid flows through the fluidic channel across the first plurality of optical channels.

18. The method of claim 12, wherein the information is indicative of a velocity of the at least one particle.

* * * * *